US012325761B2

(12) United States Patent
Cao et al.

(10) Patent No.: US 12,325,761 B2
(45) Date of Patent: Jun. 10, 2025

(54) CORN FIBER PROCESSING SYSTEM AND WET MILLED CORN STARCH PROCESSING SYSTEM USING SAME

(71) Applicant: NOVOZYMES A/S, Bagsvaerd (DK)

(72) Inventors: Yi Cao, Beijing (CN); Yongzhong Liang, Beijing (CN); Jianming Hao, Beijing (CN); Jieren Luo, Beijing (CN); Wei Li, Beijing (CN); Hua Ye, Beijing (CN)

(73) Assignee: NOVOZYMES A/S, Bagsvaerd (DK)

( * ) Notice: Subject to any disclaimer, the term of this patent is extended or adjusted under 35 U.S.C. 154(b) by 992 days.

(21) Appl. No.: 17/416,722

(22) PCT Filed: Nov. 4, 2019

(86) PCT No.: PCT/CN2019/115353
§ 371 (c)(1),
(2) Date: Dec. 20, 2021

(87) PCT Pub. No.: WO2020/125241
PCT Pub. Date: Jun. 25, 2020

(65) Prior Publication Data
US 2022/0106413 A1  Apr. 7, 2022

(30) Foreign Application Priority Data

Dec. 21, 2018  (CN) .......................... 201822167470.3

(51) Int. Cl.
*C08B 30/02*  (2006.01)
*B01D 11/02*  (2006.01)
(Continued)

(52) U.S. Cl.
CPC ............ *C08B 30/12* (2013.01); *B01D 11/028* (2013.01); *B01D 36/00* (2013.01); *C08B 30/02* (2013.01);
(Continued)

(58) Field of Classification Search
CPC ......... C08B 30/12; C08B 30/02; C08B 30/04; C08B 30/06; C08B 30/08; C12P 19/04;
(Continued)

(56) References Cited

U.S. PATENT DOCUMENTS 3,029,168 A * 4/1962 Meisel ................. B01D 29/237
127/65
3,519,431 A * 7/1970 Truman .................... B02C 9/04
426/430
(Continued)

FOREIGN PATENT DOCUMENTS

CN   102453741 A    5/2012
CN   204939355 U *  1/2016  ........... C08B 30/044
(Continued)

OTHER PUBLICATIONS

English Translation of patent publication JP 2010514910A, published May 6, 2010. (Year: 2010).*
(Continued)

*Primary Examiner* — Joseph W Drodge
(74) *Attorney, Agent, or Firm* — David A. Fazzolare

(57) ABSTRACT

The embodiments of the present application provide a maize fiber processing system and a maize wet-milled starch processing system using same. The maize fiber processing system comprises a pressure curved screen group, a fiber washing sink group, an enzyme preparation adding device and an external enzyme reaction tank, wherein the external enzyme reaction tank is used for receiving screen overflow from a middle stage of pressure curved screen or fiber slurry in a middle stage of fiber washing sink and providing a place for enzyme reaction, thereby extending reaction time of enzyme participation. In addition, the reaction efficiency of the enzyme preparation can be further improved by means of (Continued)

controlling the fiber dry substance concentration in the external enzyme reaction tank.

17 Claims, 15 Drawing Sheets

(51) Int. Cl.
 *B01D 36/00* (2006.01)
 *C08B 30/04* (2006.01)
 *C08B 30/06* (2006.01)
 *C08B 30/12* (2006.01)
 *C12P 19/04* (2006.01)
 *D06M 16/00* (2006.01)

(52) U.S. Cl.
 CPC .............. *C08B 30/04* (2013.01); *C08B 30/06* (2013.01); *C12P 19/04* (2013.01); *D06M 16/003* (2013.01)

(58) Field of Classification Search
 CPC ... D06M 16/003; C12M 35/08; B01D 11/028; B01D 11/0284; B01D 11/0288; B01D 36/00; B01D 2221/06
 See application file for complete search history.

(56) References Cited

U.S. PATENT DOCUMENTS

| | | | |
|---|---|---|---|
| 4,252,900 A * | 2/1981 | Muller | C12P 7/06 127/65 |
| 5,198,035 A | 3/1993 | Lee | |
| 2008/0279983 A1* | 11/2008 | Lohrmann | C08B 30/04 426/44 |
| 2014/0127772 A1 | 5/2014 | Kohl | |
| 2015/0240266 A1 | 8/2015 | Lee | |
| 2022/0106413 A1 | 4/2022 | Cao et al. | |

FOREIGN PATENT DOCUMENTS

| | | | | |
|---|---|---|---|---|
| CN | 106084073 A | | 11/2016 | |
| CN | 106832009 A | | 6/2017 | |
| CN | 209602429 U | | 11/2019 | |
| JP | 2010514910 A | * | 5/2010 | ........... C08B 30/046 |
| WO | 01/094608 A1 | | 12/2001 | |
| WO | 2008080566 A1 | | 7/2008 | |
| WO | 2018053220 A1 | | 3/2018 | |
| WO | 2018/095408 A1 | | 5/2018 | |

OTHER PUBLICATIONS

English Translation of Dai patent publication CN 106084073A, published Nov. 9, 2016. (Year: 2016).*
English Translation of Wang patent publication CN 204939355A, published Jan. 6, 2016. (Year: 2016).*
Li et al., 2017, China Agricultural University Press, 216-221—Tr.

* cited by examiner

CORN FIBER PROCESSING SYSTEM AND WET MILLED CORN STARCH PROCESSING SYSTEM USING SAME

CROSS-REFERENCE TO RELATED APPLICATIONS

The present application claims the right of priority for Chinese utility model patent application No. CN 201822167470.3, filed on 21 Dec. 2018 and entitled "Maize fiber processing system and maize wet-milled starch processing system using same".

TECHNICAL FIELD

The present application relates to the technical field of deep processing of maize, especially to a fiber processing device for extending enzyme reaction time during maize fiber washing, and in particular to a maize fiber processing system and a maize wet-milled starch processing system using same.

BACKGROUND ART

Maize starch is a product made from maize grains and by means of immersing same in sulfurous acid, crushing and screening same, separating and washing same, and dewatering and drying same. At present, a maize starch wet-milling method (i.e., a maize starch wet production process) is generally used in the maize starch deep processing process. The aim of maize starch production is to extract as much pure starch and as much of various by-products (such as embryos, protein, fiber, and other soluble substances) from maize grains as possible. As shown in FIG. 1, the main procedures for producing maize starch by means of the maize starch wet-milling method include the steps of maize immersion, maize crushing and embryo separation and washing, fine milling, fiber washing and drying, gluten separating, protein separating and drying, starch washing, dewatering and drying, etc.

A maize fiber washing system needs to be used during the fiber washing procedure. The maize fiber washing system is mainly composed of multiple stages of pressure curved screens, and multiple stages of fiber washing sinks cooperating with the pressure curved screens. In order to allow a slurry containing maize fiber to release more free starch, bound starch and maize protein during fiber washing, an enzyme preparation needs to be added into the fiber washing sinks to enable the enzyme preparation to perform an enzyme reaction with the slurry containing maize fiber. However, since the maize fiber stays in the fiber washing sinks for a short time, the time of a reaction in which an enzyme participates is short, the reaction is insufficient, and the efficiency of enzyme action is low.

SUMMARY OF THE INVENTION

In view of this, the present application provides a maize fiber processing system and a maize wet-milled starch processing system using same. The maize fiber processing system comprises: a pressure curved screen group, a fiber washing sink group, an enzyme preparation adding device and an external enzyme reaction tank, wherein, the pressure curved screen group has multiple stages of pressure curved screens, the pressure curved screens are used for separating fiber slurry containing starch and protein into screen overflow and screen underflow, and each stage of the pressure curved screen has a fiber slurry inlet, a screen overflow outlet and a screen underflow outlet; the fiber washing sink group is used for providing a place for washing the fiber slurry by washing water, the fiber washing sink group has multiple stages of fiber washing sinks, and each stage of the fiber washing sink has a screen overflow feeding port, a screen underflow feeding port and a discharge port; the enzyme preparation adding device is used for adding the enzyme preparation into the maize fiber processing system; and the external enzyme reaction tank is connected to a discharge port of a middle stage of fiber washing sink, the external enzyme reaction tank is used for receiving the fiber slurry in the middle stage of fiber washing sink and providing a place for enzyme reaction, the fiber slurry is returned back to the fiber slurry inlet of the next stage of pressure curved screen posterior to the middle stage of pressure curved screen through a returning pipe after predetermined time.

Preferably, the enzyme preparation adding device is an enzyme preparation adding pipe.

Preferably, the screen overflow of the pressure curved screen flows to the corresponding stage of fiber washing sink among the fiber washing sink group, and the screen underflow of the pressure curved screen flows to the non-adjacent fiber washing sink before the corresponding stage of fiber washing sink among the fiber washing sink group.

Preferably, the screen overflow of the pressure curved screen flows to the corresponding stage of fiber washing sink among the fiber washing sink group, and the screen underflow of the pressure curved screen flows to the fiber washing sink one stage or two stages apart before the corresponding stage of fiber washing sink among the fiber washing sink group.

Preferably, the middle stage of pressure curved screen refers to any stage of pressure curved screen other than the first stage of pressure curved screen and the last stage of pressure curved screen in the pressure curved screen group. More preferably, the middle stage of pressure curved screen refers to the pressure curved screen in a middle position, that is, referring to the pressure curved screen in the middle position if there are odd-numbered pressure curved screens, or referring to the first pressure curved screen in the middle position if there are even-numbered pressure curved screens.

Preferably, the middle stage of fiber washing sink refers to any stage of fiber washing sink other than the first stage of fiber washing sink and the last stage of fiber washing sink among the middle stage of fiber washing sink group. More preferably, the middle stage of fiber washing sink refers to the fiber washing sink in a middle position, that is, referring to the fiber washing sink in the middle position if there are odd-numbered fiber washing sinks, or referring to the first fiber washing sink in the middle position if there are even-numbered fiber washing sinks.

Preferably, the maize fiber processing system further has a material supply buffer tank arranged before the fiber washing sink group.

Preferably, screen underflow of the corresponding first stage of pressure curved screen flows to a gluten separating system, and screen underflow of the corresponding second stage of pressure curved screen flows to the material supply buffer tank of the maize fiber system.

Preferably, the enzyme preparation adding device is an enzyme preparation adding pipe.

Preferably, the screen underflow contains screen underflow washing water, a screen underflow washing water dividing pipe is provided in a second stage of pressure curved screen posterior to the middle stage of pressure curved screen, the screen underflow washing water dividing pipe is used for dividing part of the screen underflow washing water, so as to control dry substance concentration in the external enzyme reaction tank, the remaining screen underflow washing water is transported to the screen underflow feeding port of the middle stage of fiber washing sink, and the divided screen underflow washing water flows back into the maize fiber processing system by the screen underflow washing water dividing pipe.

Preferably, a tail end of the screen underflow washing water dividing pipe is connected to the returning pipe.

Preferably, a tail end of the screen underflow washing water dividing pipe is provided at an upper end of a final discharge port of the external enzyme reaction tank.

Preferably, a tail end of the screen underflow washing water dividing pipe is connected to the fiber slurry inlet of a next stage of pressure curved screen posterior to the middle stage of pressure curved screen.

Preferably, a starting end of the screen underflow washing water dividing pipe is provided on the pipe between the screen underflow outlet and the screen underflow feeding port.

Preferably, the maize fiber processing system further comprises: an external water storage buffer tank provided on the screen underflow washing water dividing pipe.

Preferably, the maize fiber processing system further comprises: a dry substance concentration meter, which is provided at an initial material inlet of the external enzyme reaction tank and is used for measuring the dry substance concentration of the fiber slurry in the external enzyme reaction tank.

Preferably, the external enzyme reaction tanks are batch reaction tanks, and there are at least three external enzyme reaction tanks, in which the fiber slurry is controlled by means of valves to simultaneously carry out feeding, enzyme reaction and discharging.

Preferably, at any time, the fiber slurry is fed into only one of the external enzyme reaction tanks by means of a first valve, and meanwhile, the fiber slurry is discharged out of only one of the external enzyme reaction tanks by means of a second valve.

Preferably, each of the external enzyme reaction tanks is internally provided with a stirring device.

Preferably, the external enzyme reaction tanks are continuous reaction tanks, and there are multiple external enzyme reaction tanks, which are connected in series, and each of which is internally provided with a first stirring device.

Preferably, the external enzyme reaction tank is a horizontal enzyme reaction tank, which has multiple horizontally arranged first compartments and second stirring devices corresponding to the first compartments, with the fiber slurry sequentially flowing through the first compartments.

Preferably, the external enzyme reaction tank is a vertical enzyme reaction tank, which has multiple vertically arranged second compartments and third stirring devices corresponding to the second compartments, with the fiber slurry sequentially flowing through the second compartments.

The present application further provides a maize fiber processing system and a maize wet-milled starch processing system using same. The maize fiber processing system comprises: a pressure curved screen group, a fiber washing sink group, an enzyme preparation adding device and an external enzyme reaction tank, wherein, the pressure curved screen group has multiple stages of pressure curved screens, the pressure curved screens are used for separating fiber slurry containing starch and protein into screen overflow and screen underflow, and each stage of the pressure curved screen has a fiber slurry inlet, a screen overflow outlet and a screen underflow outlet; the fiber washing sink group is used for providing a place for washing the fiber slurry by washing water, the fiber washing sink group has multiple stages of fiber washing sinks, and each stage of the fiber washing sink has a screen overflow feeding port, a screen underflow feeding port and a discharge port; the enzyme preparation adding device is used for adding the enzyme preparation into the maize fiber processing system; and the external enzyme reaction tank is connected to a screen overflow outlet of a middle stage of pressure curved screen, the external enzyme reaction tank is used for receiving the screen overflow in the middle stage of pressure curved screen and providing a place for enzyme reaction, the screen overflow is returned back to the fiber slurry inlet of a next stage of pressure curved screen posterior to the middle stage of pressure curved screen through a returning pipe after predetermined time.

Preferably, the external enzyme reaction tank has an injecting water inlet for adjusting fiber dry substance concentration in the external enzyme reaction tank.

Further, the injecting water inlet is externally connected to an injecting water pipe for adjusting fiber dry substance concentration in the external enzyme reaction tank.

Preferably, the maize fiber processing system further comprises: a first flow controlling device which is provided at the injecting water inlet and is used for controlling the amount of injecting water received by the external enzyme reaction tank.

Further, the maize fiber processing system further comprises a washing water injection adjusting device which correspondingly reduces the amount of washing water injected into the maize fiber processing system according to the amount of injecting water so as to keep the total amount of water in the maize fiber processing system unchanged.

Preferably, the maize fiber processing system further comprises: a second flow controlling device which is provided at a washing water inlet of the maize fiber processing system and is used for controlling the water inflow amount of external washing water of the maize fiber processing system.

Further, the enzyme preparation adding device is an enzyme preparation adding pipe.

Preferably, the external enzyme reaction tank is a horizontal enzyme reaction tank, which has multiple horizontally arranged first compartments and first stirring devices corresponding to the first compartments, with the fiber slurry sequentially flowing through the first compartments.

Preferably, the horizontal enzyme reaction tank has multiple vertically and alternately arranged semi-closed isolation plates, which are used for dividing the horizontal enzyme reaction tank into the multiple first compartments.

Further, the external enzyme reaction tanks are multiple continuous reaction tanks, which are connected in series, and each of which is internally provided with a second stirring device.

Preferably, the external enzyme reaction tank is a vertical enzyme reaction tank, which has multiple vertically arranged second compartments and third stirring devices corresponding to the second compartments, with the fiber slurry sequentially flowing through the second compartments.

The present application further provides a maize wet-milled starch processing system, which comprises any maize fiber processing system selected from the above particular embodiments.

Preferably, the maize wet-milled starch processing system comprises a maize crushing system, an embryo separating and washing system, a fine milling system, a fiber processing system, a fiber dewatering and drying system, a gluten separating system, a protein separating and drying system, and a starch washing, dewatering and drying system.

According to the above particular embodiments of the present application, the maize fiber processing system and the maize wet-milled starch processing system using same have at least the following beneficial effects: by means of transporting the fiber slurry in the middle stage of fiber washing sink to the external enzyme reaction tank, or by means of directly transporting the screen overflow (screen overflow fiber) of the middle stage of pressure curved screen to the external enzyme reaction tank, the time of a reaction in which the enzyme preparation is involved is extended to allow the enzyme preparation to fully participate in the reaction, improve the enzyme reaction efficiency, increase the yield of maize starch and/or maize protein, and thereby increase the economic benefits.

It should be understood that the above general description and the following particular embodiments are merely exemplary and explanatory, and do not limit the scope claimed in the present application.

BRIEF DESCRIPTION OF THE DRAWINGS

The accompanying drawings below constitute part of the specification of the present application, and illustrate exemplary embodiments of the present application. The accompanying drawings are used alongside description of the specification to explain the principle of the present application.

DESCRIPTION OF REFERENCE NUMERALS

Figure 1:
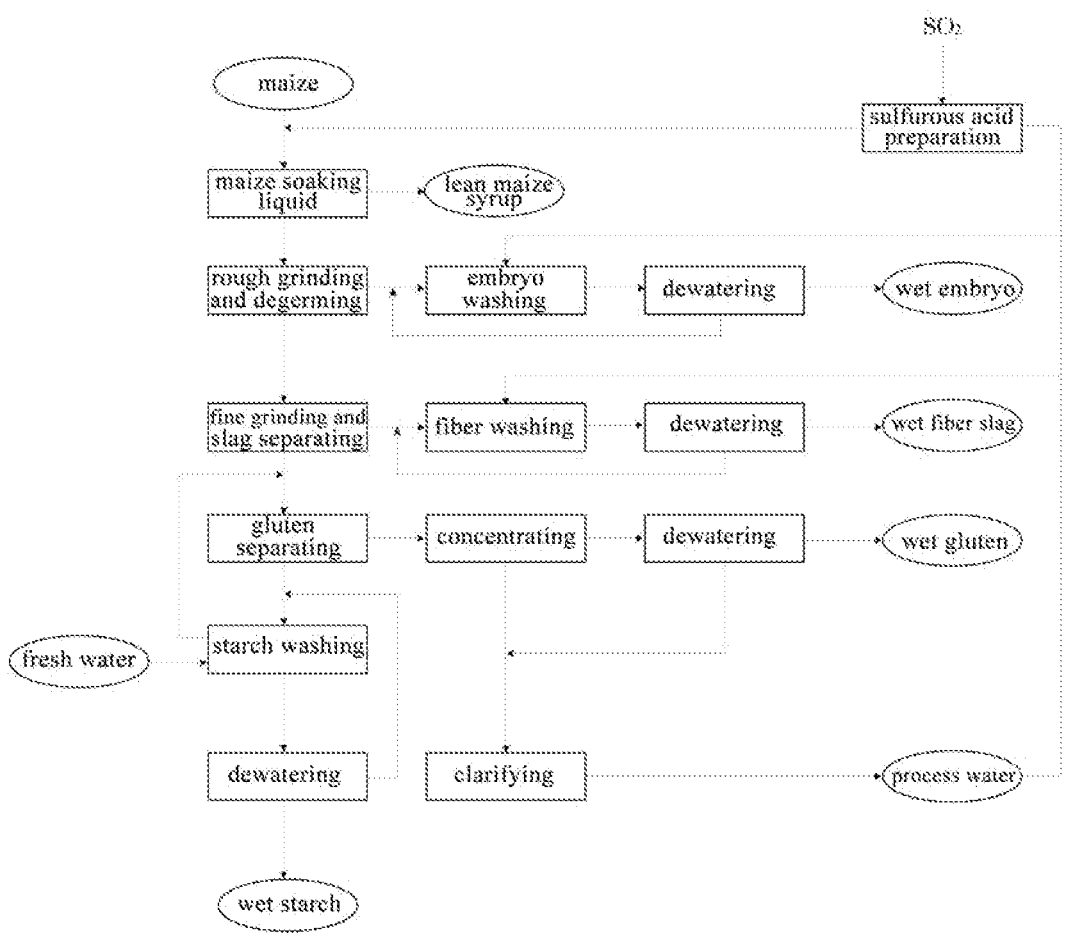
FIG. 1 is a flow diagram of maize starch wet-milling production and a cycle diagram of process water in the prior art.

| 1 | pressure curved screen group | 2 | fiber washing sink group |
|---|---|---|---|
| 3 | enzyme preparation adding device | 4 | external enzyme reaction tank |
| 5 | screen underflow washing water dividing pipe | 6 | external water storage buffer tank |
| P | pump | 11 | pressure curved screen |
| 111 | fiber slurry inlet | 112 | screen overflow outlet |
| 113 | screen underflow outlet | 21 | fiber washing sink |
| 211 | screen overflow feeding port | 212 | screen underflow feeding port |
| 213 | discharge port | 22 | material supply buffer tank |
| 11' | middle stage of pressure curved screen | 21' | middle stage of fiber washing sink |
| 41 | returning pipe | 42 | final discharge port |
| 43 | initial material inlet | 44 | valve |
| 441 | first valve | 442 | second valve |
| 45 | first stirring device | 46 | first compartment |
| 47 | second stirring device | 48 | second compartment |
| 49 | third stirring device | | |
| 1' | pressure curved screen group | 2' | fiber washing sink group |
| 3' | enzyme preparation adding device | 4' | external enzyme reaction tank |
| 5' | first flow controlling device | 6' | second flow controlling device |
| 7' | washing water inlet | 11' | pressure curved screen |
| 111' | fiber slurry inlet | 112' | screen overflow outlet |
| 113' | screen underflow outlet | 21' | fiber washing sink |
| 211' | screen overflow feeding port | 212' | screen underflow feeding port |
| 213' | discharge port | 11" | middle stage of pressure curved screen |
| 41' | returning pipe | 42' | injecting water inlet |
| 43' | injecting water pipe | 44' | first compartment |
| 45' | first stirring device | 46' | semi-closed isolation plate |
| 46' | first compartment | 47' | second stirring device |

-continued

| 48' 49B' | second compartment baffle | 49' | third stirring device |
| --- | --- | --- | --- |
| 100 | maize crushing system | 200 | embryo separating and washing system |
| 300 | fine milling system | 400 | fiber processing system |
| 500 | fiber dewatering and drying system | 600 | gluten separating system |
| 700 | protein separating and drying system | 800 | starch washing, dewatering and drying system |

DETAILED DESCRIPTION OF EMBODIMENTS

In order to make the purpose, technical solutions and advantages of the embodiments of the present application clearer, the spirit of the content disclosed in the present application will be illustrated clearly below with reference to the accompanying drawings and the detailed description. For any person skilled in the pertinent technical field, after understanding the embodiments of the content of the present application, could make changes and modifications from the technique of teaching of the contents of the present application without departing from the spirit and scope of the content of the present application.

The illustrative embodiments of the present application and the description thereof are used to explain the present application, but are not intended to limit the present application. In addition, the elements/members with the same or similar reference numerals used in the accompanying drawings and the embodiments are used to represent the same or similar portions.

The words "first", "second", . . . , etc. used herein neither specifically refer to the sequence or order, nor limit the present application, but are merely used to distinguish the elements or operations described with the same technical terms.

The directional terms used herein, such as up, down, left, right, front or back, are merely the directions with reference to the accompanying drawings. Therefore, the directional terms used are used to illustrate but not to limit this invention.

The words "including", "comprising", "having", "containing", etc. used herein are all open wording, which means including but not limited to.

The word "and/or" used herein includes any or all combinations of the mentioned things.

The word "multiple" used herein includes "two" and "more than two", and the word "multiple groups" used herein includes "two groups" and "more than two groups".

The words "roughly", "about", etc. used herein are used to modify any amount or error that may be slightly changed, which will not change the essence thereof. In general, the range of slight changes or errors modified by such words may be 20% in some of the embodiments, 10% in some of the embodiments, and 5% or other values in some of the embodiments. Those skilled in the art should understand that the values mentioned above could be adjusted according to actual needs and are not limited thereto.

In the fiber washing process, in order to release more free starch, bound starch and maize protein from the slurry containing maize fiber, it is necessary to add an enzyme preparation in the fiber processing system. The enzyme preparation may reduce the hydrophilicity of cellulose and hemicellulose, reduce the water content of fiber substance, improve the concentration and drying efficiency, reduce the amount of steam used for concentration and drying, and thereby save the energy consumption. In the prior art, an enzyme reacts with the fiber slurry in a fiber washing sink. However, since the maize fiber stays in the fiber washing sinks for a short time, the time of a reaction in which an enzyme participates is short, the reaction is insufficient, and the efficiency of enzyme action is low.

In a preferred embodiment of the present application, an external enzyme reaction tank is provided in a middle stage of fiber washing sink to receive fiber slurry in the middle stage of fiber washing sink, and the fiber slurry stays in the external enzyme reaction tank for predetermined time (for example, the contact reaction time distribution of most fiber slurry in the external enzyme reaction tank is 90 minutes to 240 minutes, and the average contact reaction time is 150 minutes). While the fiber slurry stays in the external enzyme reaction tank, the enzyme continues to react with the fiber slurry in the external enzyme reaction tank, and the fiber slurry is returned back from the external enzyme reaction tank to a fiber slurry inlet of a next stage of pressure curved screen posterior to the middle stage of pressure curved screen after predetermined time, which can effectively extend the time of a reaction in which the enzyme preparation participate, allow the enzyme preparation to fully participate in the reaction, minimize the hydrophilicity of the cellulose and the hemicellulose, improve the yield of starch, improve the reaction efficiency of the enzyme preparation and reduce the wastewater generated in the wet-milled maize starch production.

In addition, in an existing maize wet-milled fiber water washing process, the screen overflow fiber from the corresponding stage of pressure curved screen and the screen underflow washing water from the later two stages of pressure curved screen may converge in the fiber washing sink, and the fiber dry substance concentration of the fiber slurry in the fiber washing sink cannot be freely adjusted.

The fiber dry substance concentration may affect the performance of the enzyme preparation. In a preferred embodiment of the present application, in order to obtain the optimum performance, the fiber dry substance concentration during the enzyme preparation reaction should be 4%-6% (with non-fiber dry substances in the fiber slurry being washed off with a 75 micron screen), because a lower fiber dry substance concentration will lead to a lower enzyme performance, while a higher fiber dry substance concentration will lead to the increase in viscosity, which is not conducive to continuous operation of the material in the system.

In a preferred embodiment of the present application, a screen underflow washing water dividing pipe is provided in a second stage of pressure curved screen posterior to the middle stage of pressure curved screen, and the screen underflow washing water dividing pipe is used for dividing part of the screen underflow washing water, for example, allowing part of washing water to bypass the external enzyme reaction tank without mixing with the fiber slurry. The flow of divided washing water is controlled by a valve so as to have a function of adjusting the fiber dry substance concentration in the external enzyme reaction tank to adjust the dry substance concentration of a fiber mixture in the external enzyme reaction tank and further improve the action of the enzyme.

In a preferred embodiment of the present application, taking an existing process in factory as an example, the screen overflow fiber dry substance content of the previous stage of pressure curved screen is about 7%-8%, and the flow thereof is 40 m³/h; the flow of the screen underflow washing water of the later stage of pressure curved screen is 110 m³/h; and after mixing, the fiber dry substance concentration in the external enzyme reaction tank is about 2%, and if the washing water of 70 m³/h is divided to allow the washing water of 40 m³/h to enter the external enzyme reaction tank and be mixed with a fiber material, the fiber dry substance concentration in the external enzyme reaction tank can be increased to 3.5%-4%, such that the enzyme preparation has a better reaction performance.

In a preferred embodiment of the present application, the middle stage of pressure curved screen specifically refers to the pressure curved screen, in the pressure curved screen group, other than the pressure curved screens on two sides, that is, refers to any pressure curved screen other than the leftmost pressure curved screen and the rightmost pressure curved screen. A screen overflow outlet of the middle stage of pressure curved screen is connected to the external enzyme reaction tank, the screen overflow outlet of the middle stage of pressure curved screen may no longer be in communication with a screen overflow feeding port of the corresponding fiber washing sink, or a valve may be additionally provided on a pipe between the screen overflow outlet of the middle stage of pressure curved screen and the screen overflow feeding port of the corresponding fiber washing sink so as to use the valve to cut off the communication between the screen overflow outlet of the middle stage of pressure curved screen and the screen overflow feeding port of the corresponding fiber washing sink.

In a preferred embodiment of the present application, screen overflow in the middle stage of pressure curved screen can be transferred out of a maize fiber processing system for enzyme reaction, the screen overflow can be returned back to the fiber slurry inlet of the next stage of pressure curved screen posterior to the middle stage of pressure curved screen through a returning pipe after predetermined time, and then the screen overflow is returned back to the maize fiber processing system. The time of the reaction in which the enzyme preparation participates may be extended to allow the enzyme preparation to fully react to improve the action efficiency of the enzyme preparation.

In a preferred embodiment of the present application, the screen overflow outlet of the middle stage of pressure curved screen can be connected to the external enzyme reaction tank, and the screen overflow in the middle stage of pressure curved screen can be transferred to an external enzyme reaction tank outside the maize fiber processing system for enzyme reaction, such that the relative yield of starch and protein is high without considering the continuous operation performance of materials in the system.

In the existing maize wet-milled fiber water washing process, the screen overflow fiber (screen overflow) from the corresponding stage of pressure curved screen and the screen underflow washing water (screen underflow) from the pressure curved screen two stages posterior to the same can converge in the fiber washing sink, and the fiber dry substance concentration of the fiber slurry in the fiber washing sink cannot be freely adjusted. The fiber dry substance concentration may affect the performance of the enzyme preparation, because a lower fiber dry substance concentration will lead to a lower enzyme performance of the enzyme preparation, while a higher fiber dry substance concentration will lead to the increase in viscosity, which is not conducive to the continuous operation of the material (specifically the screen overflow or the screen overflow fiber) in the system.

In a preferred embodiment of the present application, in order to achieve the optimum performance, washing water can directly flow into the external enzyme reaction tank, and the fiber dry substance concentration during the enzyme preparation reaction can be adjusted to 4%-6% (with the non-fiber dry substance in the fiber slurry being washed off with a 75 micron screen).

In a preferred embodiment of the present application, taking the existing process in factory as an example, the screen overflow fiber dry substance content of the previous stage of pressure curved screen is about 7%-8%, and the flow thereof is 40 m³/h, and if the washing water of 30 m³/h is introduced into the external enzyme reaction tank to dilute screen overflow in the external enzyme reaction tank, the fiber dry substance concentration in the external enzyme reaction tank can be adjusted to 5.24%-6%, such that the enzyme preparation has a better reaction performance.

The enzyme reaction time can be calculated by means of dividing the effective volume of the external enzyme reaction tank by the total flow of the fiber slurry, with the total flow of the fiber slurry including the fiber flow (screen overflow flow) and the washing water flow (screen underflow flow). By means of dividing part of the washing water flow, the total flow into the enzyme reaction tank is reduced, such that the enzyme reaction time can be extended without changing the effective volume of the external enzyme reaction tank.

Embodiment 1

Figure 2:
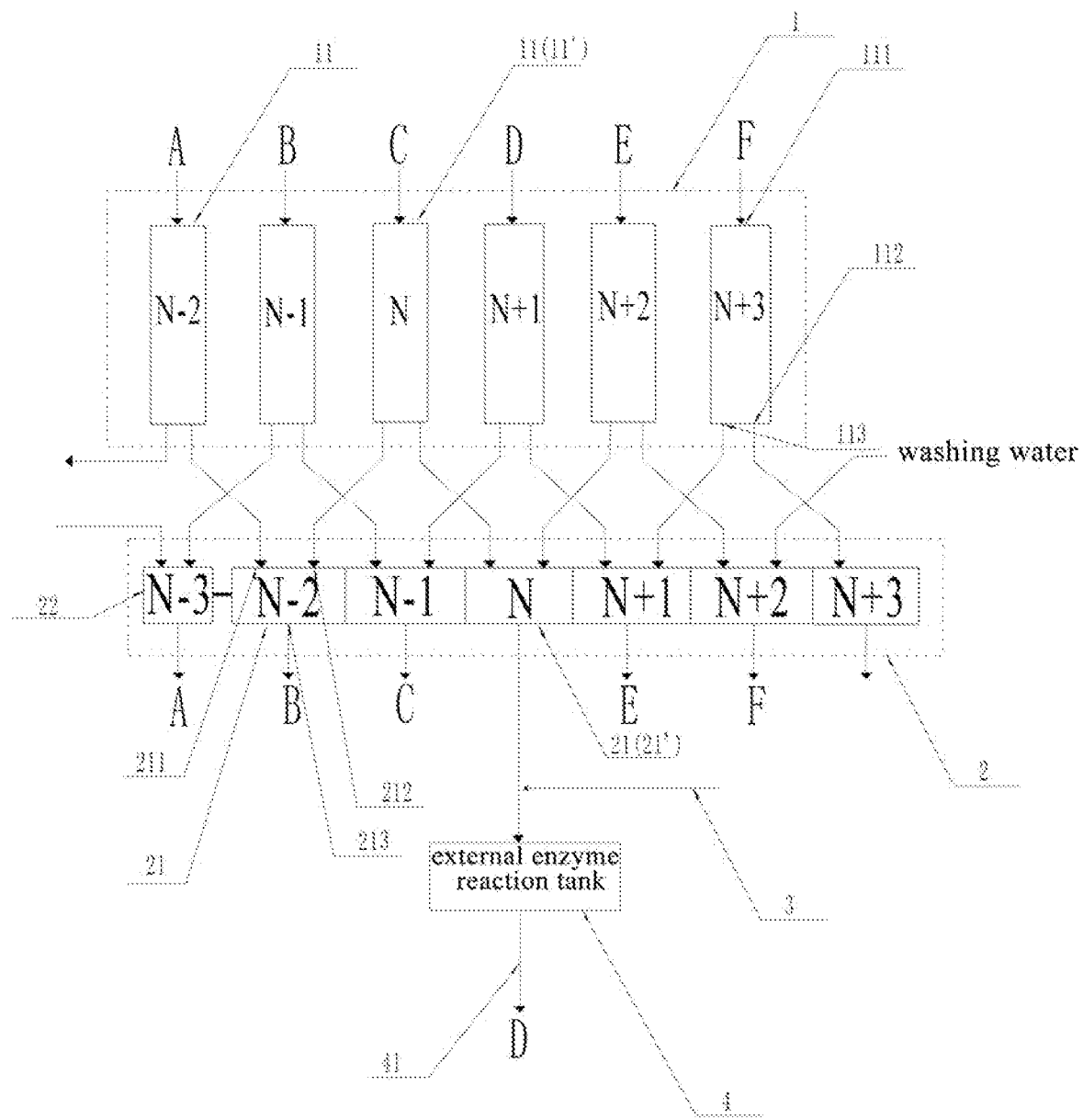
FIG. 2 is a structural schematic diagram of a maize fiber processing system for extracting maize starch provided in a particular embodiment of the present application.

With reference to FIG. 2, a maize fiber processing system for extracting maize starch may comprise: a pressure curved screen group 1, a fiber washing sink group 2, an enzyme preparation adding device 3 and an external enzyme reaction tank 4. The pressure curved screen group 1 matches the fiber washing sink group 2.

The pressure curved screen group 1 has multiple stages of pressure curved screens 11, the pressure curved screens 11 are used for separating fiber slurry containing starch and protein into screen overflow and screen underflow, and each stage of the pressure curved screen 11 has a fiber slurry inlet 111, a screen overflow outlet 112 and a screen underflow outlet 113. For ease of description, it is assumed that the pressure curved screen group 1 has six stages of pressure curved screens 11, including a pressure curved screen N−2 (the corresponding first stage of pressure curved screen), a pressure curved screen N−1 (the corresponding second stage of pressure curved screen), a pressure curved screen N (i.e., a middle stage of pressure curved screen), a pressure curved screen N+1 (i.e., a next stage of pressure curved screen posterior to the middle stage of pressure curved screen), a pressure curved screen N+2 (i.e., a second stage of pressure curved screen posterior to the middle stage of pressure curved screen), and a pressure curved screen N+3 (i.e., a third stage of pressure curved screen posterior to the middle stage of pressure curved screen). The screen overflow mainly comprises wet fiber, attached starch and protein, etc., and the screen underflow mainly comprises screen underflow washing water, starch, protein, etc. The first stage of screen underflow (the screen underflow output from a screen underflow outlet 113 of the pressure curved screen N−2) is crude starch milk, the second stage of screen underflow (the screen underflow output from a screen underflow outlet 113 of the pressure curved screen N−1) comes from screen underflow separated from the previous stage of pressure curved screen (the pressure curved screen N), and starch milk concentration is getting lower and lower. Preferably, the middle stage of pressure curved screen refers to any stage of pressure curved screen other than the first stage of pressure curved screen and the last stage of pressure curved screen in the pressure curved screen group. More preferably, the middle stage of pressure curved screen refers to the pressure curved screen in a middle position, that is, referring to the pressure curved screen in the middle position if there are odd-numbered pressure curved screens, or referring to the first pressure curved screen in the middle position if there are even-numbered pressure curved screens. As shown in FIG. 2, the middle stage of pressure curved screen refers to the pressure curved screen N.

Further, the screen underflow of the corresponding first stage of pressure curved screen 11 flows to a gluten separating system, and the screen underflow of the corresponding second stage of pressure curved screen 11 flows to a material supply buffer tank 22 of a maize fiber system.

In a particular embodiment of the present application, the pressure curved screen 11 is used for separating the fiber slurry containing starch and protein into the screen overflow and the screen underflow, the screen overflow of the pressure curved screen 11 flows to the corresponding stage of fiber washing sink 21 among the fiber washing sink group 2 through the screen overflow outlet 112, the screen underflow of the pressure curved screen 11 flows to the fiber washing sink 21 before the corresponding stage of fiber washing sink 21 among the fiber washing sink group 2 through the screen underflow outlet 113, and the fiber washing sink 21 connected to the screen overflow outlet 112 of the pressure curved screen 11 is not adjacent to, preferably one stage or two stages of fiber washing sinks 21 apart from, the fiber washing sink 21 connected to the screen underflow outlet 113 of the pressure curved screen 11. In a preferred embodiment of the present application, the screen underflow of the pressure curved screen 11 flows to a small material compartment of the fiber washing sink 21 which is supplied with the material by the pressure curved screen among the fiber washing sink group 2 through the screen underflow outlet 113, and overflows to the previous fiber washing sink 21 through the small material compartment.

In a preferred embodiment of the present application, the fiber washing sink 21 connected to the screen overflow outlet 112 of the pressure curved screen 11 is one stage or two stages of fiber washing sinks 21 apart from the fiber washing sink 21 connected to the screen underflow outlet 113 of the pressure curved screen 11. As shown in FIG. 2, the fiber washing sink 21 connected to the screen overflow outlet 112 of the pressure curved screen 11 is one stage of fiber washing sink 21 apart from the fiber washing sink 21 connected to the screen underflow outlet 113 of the pressure curved screen 11, and the pressure curved screen N−2 supplies the screen overflow fiber dry substance to the fiber washing sink N−2, and supplies the screen underflow washing water to the gluten separating system later. The pressure curved screen N−1 supplies the screen overflow fiber dry substance to the fiber washing sink N−1, and supplies the screen underflow washing water to a front-placed washing sink N−3 (i.e., the material supply buffer tank) later. The pressure curved screen N supplies the screen overflow fiber dry substance to the fiber washing sink N, and supplies the screen underflow washing water to the fiber washing sink N−2 later. The pressure curved screen N+1 supplies the screen overflow fiber dry substance to the fiber washing sink N+1, and supplies the screen underflow washing water to the fiber washing sink N−1 later. The pressure curved screen N+2 supplies the screen overflow fiber dry substance to the fiber washing sink N+2, and supplies the screen underflow washing water to the fiber washing sink N later. The pressure curved screen N+3 supplies the screen overflow fiber dry substance to the fiber washing sink N+3, and supplies the screen underflow washing water to the fiber washing sink N+1 later.

The above is merely one embodiment of the present application, and the pressure curved screen group 1 and the fiber washing sink group 2 may also match in the way as follows: the fiber washing sink 21 connected to the screen overflow outlet 112 of the pressure curved screen 11 is two stages of fiber washing sinks 21 apart from the fiber washing sink 21 connected to the screen underflow outlet 113 of the pressure curved screen 11, and the pressure curved screen N−2 supplies the screen overflow fiber dry substance to the fiber washing sink N−2, and supplies the screen underflow washing water to the gluten separating system later. The pressure curved screen N−1 supplies the screen overflow fiber dry substance to the fiber washing sink N−1, and supplies the screen underflow washing water to the gluten separating system later. The pressure curved screen N supplies the screen overflow fiber dry substance to the fiber washing sink N, and supplies the screen underflow washing water to the front-placed washing sink N−3 later. The pressure curved screen N+1 supplies the screen overflow fiber dry substance to the fiber washing sink N+1, and supplies the screen underflow washing water to the fiber washing sink N−2 later. The pressure curved screen N+2 supplies the screen overflow fiber dry substance to the fiber washing sink N+2, and supplies the screen underflow washing water to the fiber washing sink N−1 later. The pressure curved screen N+3 supplies the screen overflow fiber dry substance to the fiber washing sink N+3, and supplies the screen underflow washing water to the fiber washing sink N later, which are not limited thereto in the present application.

The fiber washing sink group 2 is used for providing a place for washing the fiber slurry by washing water, the fiber washing sink group 2 has multiple stages of fiber washing sinks 21, and each stage of the fiber washing sink 21 has a screen overflow feeding port 211, a screen underflow feeding port 212 and a discharge port 213. In the same way, for ease of description, it is assumed that the fiber washing sink group 2 has six stages of fiber washing sinks 21, including the fiber washing sink N−2, the fiber washing sink N−1, the fiber washing sink N (i.e., a middle stage of fiber washing sink), the fiber washing sink N+1, the fiber washing sink N+2, and the fiber washing sinks N+3. Preferably, the middle stage of fiber washing sink refers to any stage of fiber washing sink other than the first stage of fiber washing sink and the last stage of fiber washing sink among the middle stage of fiber washing sink group. More preferably, the middle stage of fiber washing sink refers to a fiber washing sink in a middle position. If there are odd-numbered fiber washing sinks, the middle stage of fiber washing sink refers to the fiber washing sink in the middle position; and if there are even-numbered fiber washing sinks, the middle stage of fiber washing sink refers to the first fiber washing sink in the middle position.

Further, for the temporary storage of the fiber slurry and the better control of the fiber washing process, the front end of the fiber washing sink N−2 can be further provided with a front-placed washing sink N−3. The front-placed washing sink N−3 is also referred to as the material supply buffer tank 22, and receives the screen underflow of the corresponding second stage of pressure curved screen 11 (i.e., the pressure curved screen N−1) and the fiber material produced by a fine milling system, and the screen underflow and the fiber material are thoroughly mixed in the material supply buffer tank 22 to form the fiber slurry. In order to realize countercurrent washing of maize fiber, the pressure curved screen group 1 and the fiber washing sink group 2 are arranged cooperatively, the fiber slurry output from the discharge port 213 of the fiber washing sink 21 is transported to the next stage of pressure curved screen 11, the fiber dry substance output from the screen overflow outlet 112 of the pressure curved screen 11 is transported to the corresponding fiber washing sink 21, the screen underflow washing water output from the screen underflow outlet 113 of the pressure curved screen 11 is transported to two higher stages of fiber washing sinks 21, thus realizing the movement of the fiber dry substance from a lower stage of fiber washing sink 21 to a higher stage of fiber washing sink 21, and the movement of the screen underflow washing water from the higher stage of fiber washing sink 21 to the lower stage of fiber washing sink 21, thereby realizing countercurrent washing of maize fiber. For example, the fiber slurry output from the discharge port 213 of the fiber washing sink N+2 is transported to the pressure curved screen N+3, the screen overflow fiber dry substance output from the screen overflow outlet 112 of the pressure curved screen N+3 is transported to the fiber washing sink N+3, and the screen underflow washing water output from the screen underflow outlet 113 of the pressure curved screen N+3 is transported to the fiber washing sink N+1.

The enzyme preparation adding device 3 is used for adding the enzyme preparation to the maize fiber processing system. The enzyme preparation reacts with the fiber slurry, such that the fiber slurry releases more free starch, bound starch and maize protein. The enzyme preparation adding device 3 may be an enzyme preparation adding pipe, and the enzyme preparation adding pipe 3 may be connected to an input pipe of the external enzyme reaction tank 4, as shown in FIG. 2. In addition, the enzyme preparation adding pipe 3 may also be connected to an input pipe of the middle stage of fiber washing sink 21', and the enzyme preparation adding pipe 3 may also be connected to the middle stage of fiber washing sink 21'. The enzyme preparation may be manually added through the enzyme preparation adding pipe 3, and may be added through the enzyme preparation adding pipe 3 by means of a pump, which is not limited thereto in the present application.

The external enzyme reaction tank 4 is connected to the discharge port 213 of the middle stage of fiber washing sink 21', the external enzyme reaction tank 4 is used for receiving the fiber slurry in the middle stage of fiber washing sink 21' and providing a place for enzyme reaction. The fiber slurry in the external enzyme reaction tank 4 is returned back to the fiber slurry inlet 111 of a next stage of pressure curved screen 11 posterior to the middle stage of pressure curved screen 11' through the returning pipe 41 after predetermined time. According to the requirements for equipment space and fiber slurry retention time, the external enzyme reaction tank 4 may be one tank or a combined tank formed of multiple tanks. The specific form of the external enzyme reaction tank 4 will be illustrated in the following embodiments, which will not be repeated herein in view of the length. As shown in FIG. 2, it is assumed that the fiber washing sink group 2 has six stages of fiber washing sinks 21, the pressure curved screen group 1 has six stages of pressure curved screens 11, the middle stage of fiber washing sink 21' is the fiber washing sink N, the middle stage of pressure curved screen 11' is the pressure curved screen N, and the next stage of pressure curved screen 11 posterior to the middle stage of pressure curved screen 11' is the pressure curved screen N+1.

In addition, in order to allow the fiber slurry to smoothly flow in the external enzyme reaction tank 4, a pump may be provided at an initial material inlet 43 and/or the returning pipe 41 of the external enzyme reaction tank 4 to promote the flowing of the fiber slurry.

Embodiment 2

Figure 3:
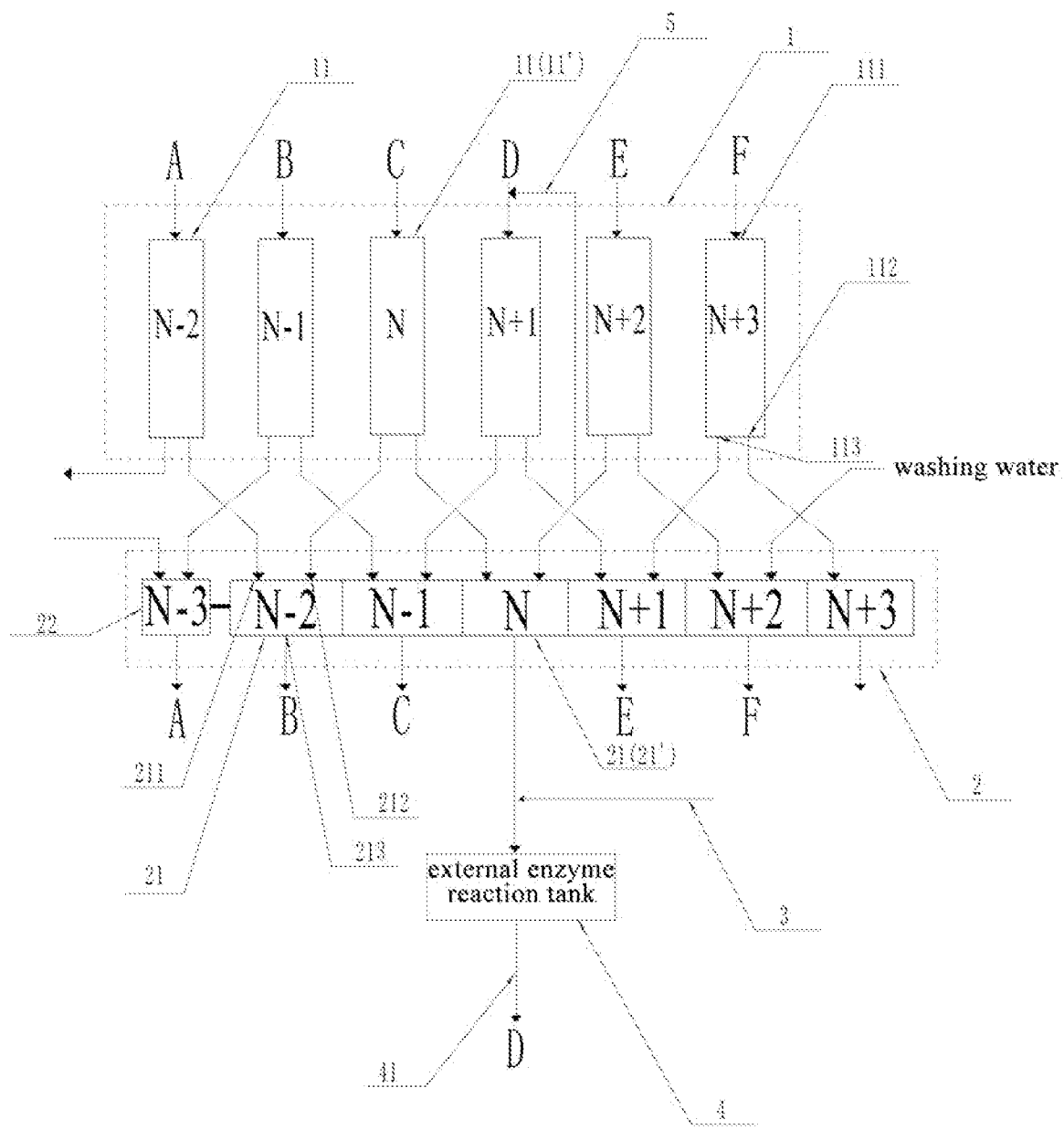
FIG. 3 is a structural schematic diagram of a maize fiber processing system for extracting maize starch provided in a particular embodiment of the present application.

With reference to FIG. 3, the fiber dry substance concentration of fiber slurry may affect the performance of enzyme preparation, and in order to achieve a better performance of the enzyme preparation, the fiber dry substance concentration should be 4%-6% (with the non-fiber dry substance in the fiber slurry being washed off with a 75 micron screen). A lower fiber dry substance concentration may lead to a lower enzyme performance, while a higher fiber dry substance concentration may lead to the increased viscosity of the fiber slurry, which is not conducive to continuous operation of the fiber slurry in a fiber processing system. Therefore, controlling the fiber dry substance concentration of the fiber slurry is conducive to further improvement of the enzyme performance. According to the above description of Embodiment 1, the fiber slurry in a middle stage of fiber washing sink 21' is directly transported to an external enzyme reaction tank, and the fiber dry substance concentration of the fiber slurry in the external enzyme reaction tank is about 2%. Although the reaction time of the enzyme preparation is extended, the fiber dry substance concentration of the fiber slurry in the external enzyme reaction tank is lower than 4%, which may not achieve better performance of the enzyme preparation.

In this embodiment, a second stage of pressure curved screen 11 posterior to a middle stage of pressure curved screen 11' is provided with a screen underflow washing water dividing pipe 5, the screen underflow washing water dividing pipe 5 is used for dividing part of screen underflow washing water, so as to control the dry substance concentration (the fiber dry substance concentration) in the external enzyme reaction tank 4, the remaining screen underflow washing water is transported to the middle stage of fiber washing sink 21', and the divided screen underflow washing water flows back into the maize fiber processing system through the screen underflow washing water dividing pipe 5. Since the fiber slurry in the middle stage of fiber washing sink 21' is transported to the external enzyme reaction tank 4, the screen underflow washing water originally transported to the external enzyme reaction tank 4 through the middle stage of fiber washing sink 21' is divided by the screen underflow washing water dividing pipe 5, such that the dry substance concentration of the fiber slurry in the external enzyme reaction tank 4 is 4%-6%, and the enzyme preparation is in a preferred reaction state. The dividing ratio of the screen underflow washing water is determined by the screen overflow fiber dry substance content and flow of the previous stage of pressure curved screen and the screen underflow washing water flow of the next stage of pressure curved screen. In order to not change the dry substance concentration of the fiber slurry of the stages other than the middle stage in the original maize fiber processing system, the screen underflow washing water divided by the screen underflow washing water dividing pipe 5 converge with the fiber slurry in the reaction tank at an outlet of the external enzyme reaction tank, so as to finally return to the maize fiber processing system.

Figure 4:
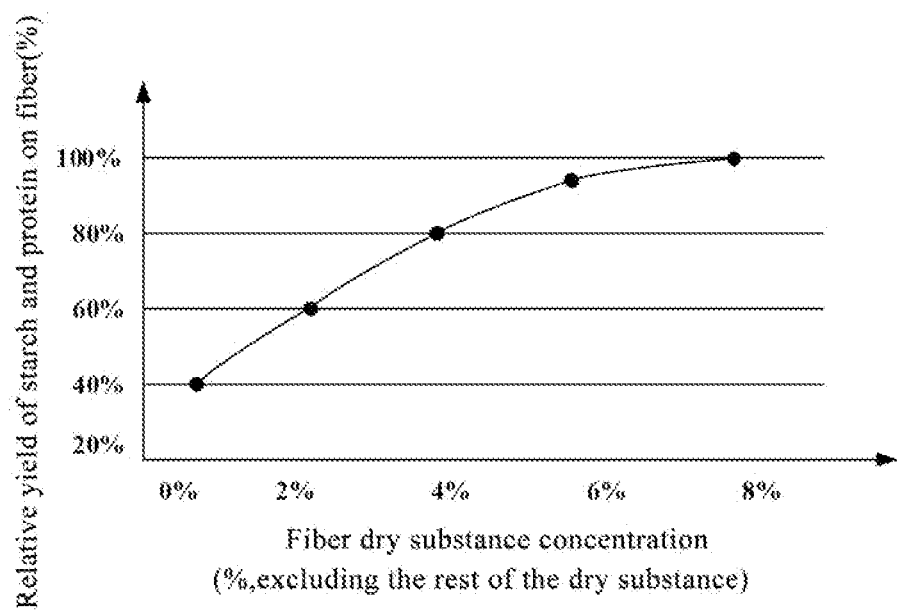
FIG. 4 is a curve graph showing the relationship between fiber dry substance concentration and the relative yield of starch and protein on fiber provided in a particular embodiment of the present application.

FIG. 4 is a curve graph showing the relationship between fiber dry substance concentration and the relative yield of starch and protein on fiber. It can be seen from FIG. 4 that the relative yield of starch and protein on fiber is 80% or higher when the fiber dry substance concentration is 4%-6%.

The specific calculation method for the above fiber dry substance concentration comprises: taking 200 g of fiber slurry from the external enzyme reaction tank, washing the fiber slurry with water on a 75 micron screen to wash off the dry substance other than fiber, then drying the screen overflow fiber in a 105° C. oven to an absolute dry weight, weighing, and dividing the absolution dry weight by the total weight of 200 g to calculate the fiber dry substance concentration.

Further, the screen underflow washing water dividing pipe 5 may be provided on a screen underflow washing water output pipe of any stage of pressure curved screen 11 posterior to the middle stage of pressure curved screen 11', as long as the screen underflow washing water discharged from a screen underflow outlet 113 of the such stage of pressure curved screen 11 is transported to the middle stage of fiber washing sink 21'. Preferably, the screen underflow washing water of the pressure curved screen 11 is transported to the corresponding stage of fiber washing sink 21, the screen overflow fiber dry substance of the pressure curved screen 11 is transported to the fiber washing sink 21 before the corresponding stage of fiber washing sink 21, and the corresponding stage of fiber washing sink 21 of the pressure curved screen 11 is at least one stage of fiber washing sink apart from the fiber washing sink 21 before the corresponding stage of fiber washing sink 21 of the pressure curved screen 11. The screen underflow washing water dividing pipe 5 is provided on the screen underflow washing water output pipe of the pressure curved screen 11 posterior to the middle stage of pressure curved screen 11', the screen underflow washing water of the pressure curved screen 11 is transported to the middle stage of fiber washing sink 21', and the screen underflow washing water dividing pipe 5 is used for dividing part of the screen underflow washing water so as to control the fiber dry substance concentration of the external enzyme reaction tank 4. The remaining screen underflow washing water is transported to the middle stage of fiber washing sink 21', and the divided screen underflow washing water flows back into the maize fiber processing system through the screen underflow washing water dividing pipe 5.

More preferably, the screen underflow washing water of the pressure curved screen 11 is transported to the corresponding stage of fiber washing sink 21, the screen overflow dry substance of the pressure curved screen 11 is transported to the fiber washing sink 21 before the corresponding stage of fiber washing sink 21, and the corresponding stage of fiber washing sink 21 of the pressure curved screen 11 is one stage of fiber washing sink 21 apart from the fiber washing sink 21 before the corresponding stage of fiber washing sink 21 of the pressure curved screen 11. The screen underflow washing water dividing pipe 5 is provided on a screen underflow washing water output pipe of the second stage of pressure curved screen 11 posterior to the middle stage of pressure curved screen 11', the screen underflow washing water of the pressure curved screen 11 is transported to the middle stage of fiber washing sink 21', and the screen underflow washing water dividing pipe 5 is used for dividing part of the screen underflow washing water so as to control the dry substance concentration of the external enzyme reaction tank 4. The remaining screen underflow washing water is transported to the middle stage of fiber washing sink 21', and the divided screen underflow washing water flows back into the maize fiber processing system through the screen underflow washing water dividing pipe 5.

One screen underflow washing water dividing pipe 5 is mounted on a screen underflow washing water conveying pipe of the second stage of pressure curved screen 11 posterior to the middle stage of pressure curved screen 11', such that part of the washing water bypasses the external enzyme reaction tank 4 without mixing with the screen overflow fiber dry substance output from a screen overflow outlet 112 of the middle stage of fiber washing sink 21', and the divided washing water flow is controlled by a valve, so as to have the function of adjusting the fiber dry substance concentration of the external enzyme reaction tank 4.

Figure 5:
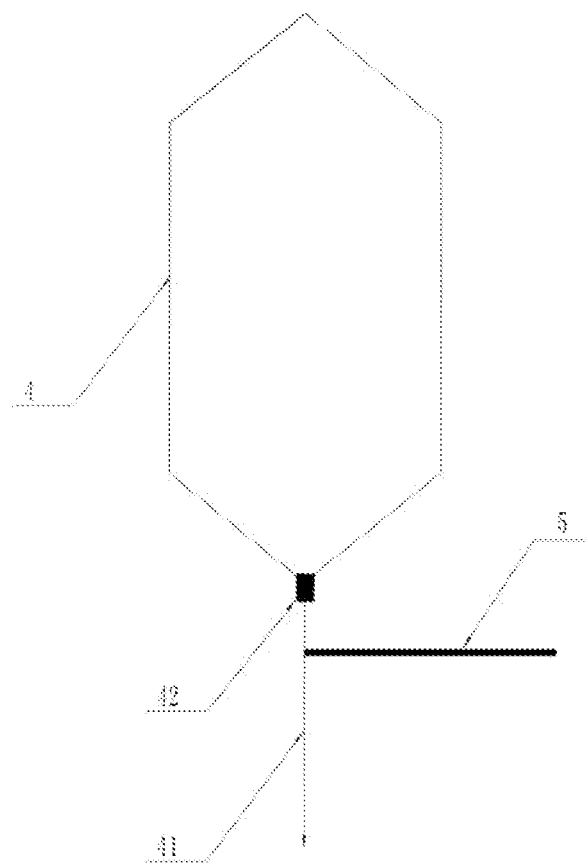
FIG. 5 is a structural schematic diagram of a connection of a tail end of a screen underflow washing water dividing pipe to a returning pipe provided in a particular embodiment of the present application.
Figure 6:
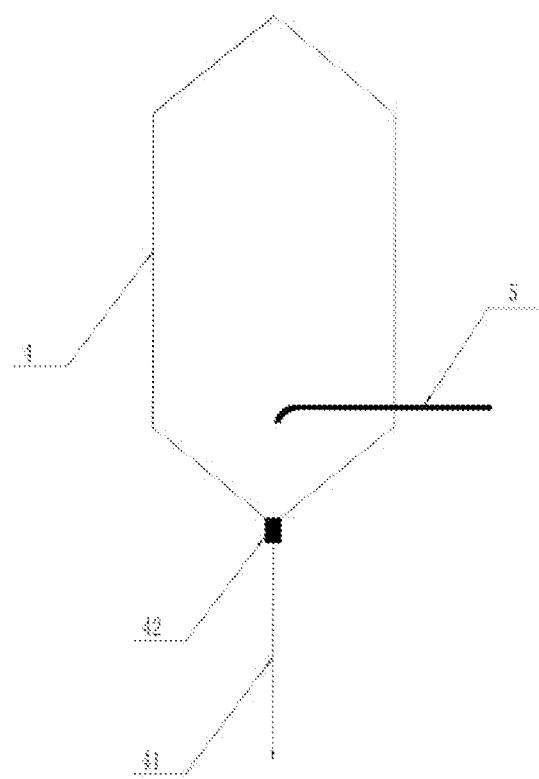
FIG. 6 is a structural schematic diagram of an arrangement of a tail end of a screen underflow washing water dividing pipe at an upper end of a final discharge port of an external enzyme reaction tank provided in a particular embodiment of the present application.

The screen underflow washing water divided by the screen underflow washing water dividing pipe 5 can flow back into the maize fiber processing system at different positions of the maize fiber processing system. The screen underflow washing water of the pressure curved screen 11 is divided by the starting end of the screen underflow washing water dividing pipe 5, and the tail end of the screen underflow washing water dividing pipe 5 allows the divided screen underflow washing water to flow back to the maize fiber processing system. The tail end of the screen underflow washing water dividing pipe 5 may be connected to the returning pipe 41 of the external enzyme reaction tank 4, the divided screen underflow washing water is transported to the returning pipe 41, and the divided screen underflow washing water flows back into the maize fiber processing system, as shown in FIG. 5. The tail end of the screen underflow washing water dividing pipe 5 may be arranged at an upper end of a final discharge port 42 of the external enzyme reaction tank 4, and the divided screen underflow washing water is discharged out of the external enzyme reaction tank 4 together with the fiber slurry in the external enzyme reaction tank 4, and is then transported to the next stage of pressure curved screen 11 posterior to the middle stage of pressure curved screen 11'. In the process of discharging the fiber slurry out of the external enzyme reaction tank 4, the divided screen underflow washing water may be thoroughly mixed with the fiber slurry in the external enzyme reaction tank 4, as shown in FIG. 6. The tail end of the screen underflow washing water dividing pipe 5 may also be connected to a fiber slurry inlet 111 of the next stage of pressure curved screen 11 posterior to the middle stage of pressure curved screen 11', such that the divided screen underflow washing water is directly transported to the next stage of pressure curved screen 11 posterior to the middle stage of pressure curved screen 11', that is, the divided screen underflow washing water is directly transported to the fiber slurry inlet 111 of the pressure curved screen N+1, as shown in FIG. 3.

Embodiment 3

Figure 7:
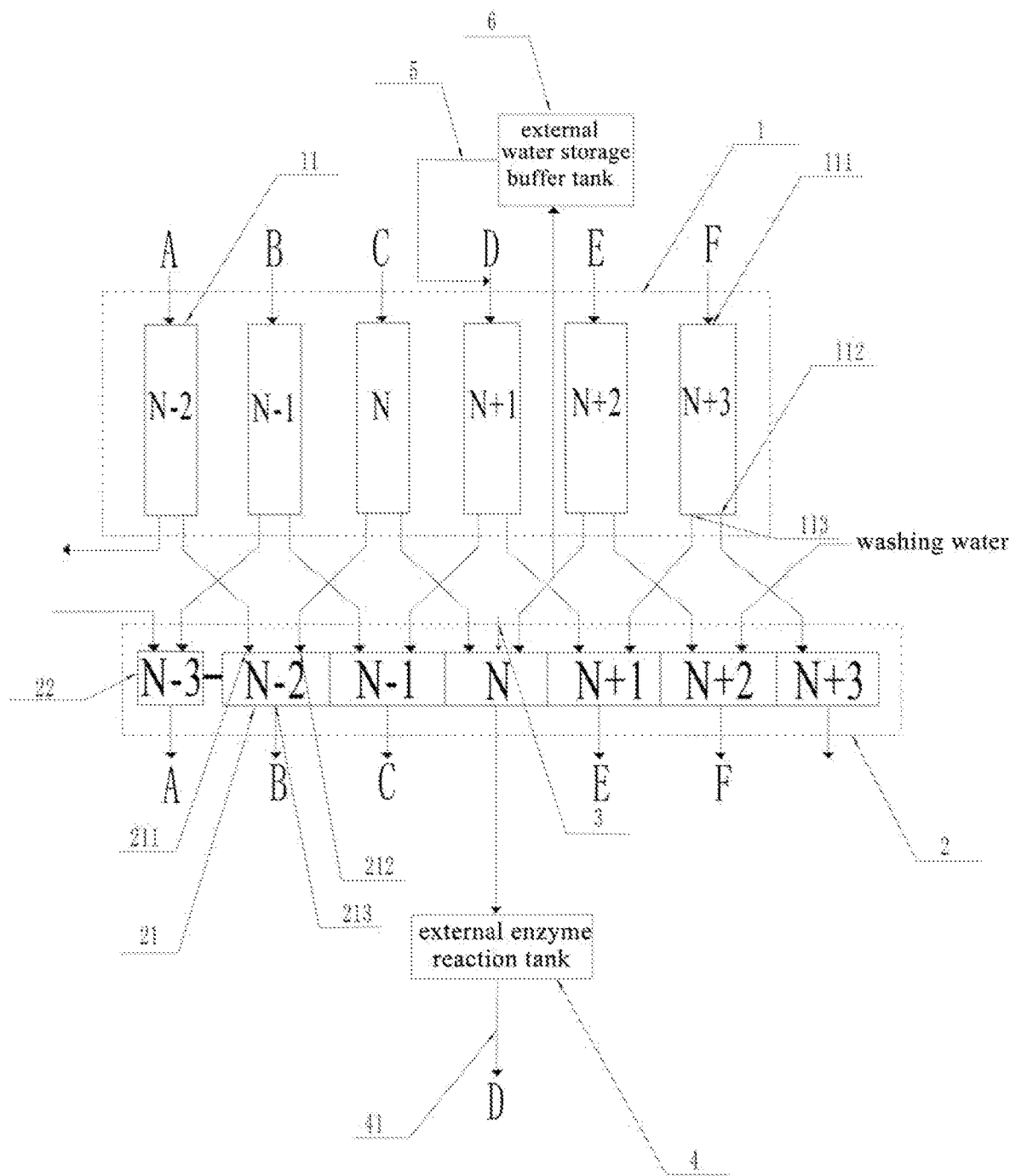
FIG. 7 is a structural schematic diagram of a maize fiber processing system for extracting maize starch provided in a particular embodiment of the present application.

As shown in FIG. 7, in order to effectively buffer the screen underflow washing water divided by a screen underflow washing water dividing pipe 5, the screen underflow washing water dividing pipe 5 may be provided with an external water storage buffer tank 6. The external water storage buffer tank 6 can temporarily store the screen underflow washing water divided by the screen underflow washing water dividing pipe 5, such that the dry substance concentration of the fiber slurry in the external enzyme reaction tank 4 can be effectively controlled when the screen underflow washing water flow of the later stage of pressure curved screen is relatively large. The screen underflow washing water of a pressure curved screen 11 is divided by the screen underflow washing water dividing pipe 5, and the proportion of the screen underflow washing water is determined by the screen overflow fiber dry substance content and flow of the previous stage of pressure curved screen and the screen underflow washing water flow of the later stage of pressure curved screen.

Embodiment 4

In the maize fiber processing system in Embodiment 1 and Embodiment 2 of the present application, the screen overflow fiber dry substance from the previous stage of pressure curved screen 11 and the screen underflow washing water from the later stage of pressure curved screen 11 converge in an external enzyme reaction tank 4, and are evenly mixed to achieve a relatively stable fiber dry substance concentration. According to the present application, the proportion of the screen underflow washing water divided by the screen underflow washing water dividing pipe 5 according to the fiber dry substance concentration can be adjusted, such that the dry substance concentration of fiber slurry in the external enzyme reaction tank 4 can be maintained at 4%-6%, and the enzyme preparation is in a preferred reaction state.

Further, the proportion of the screen underflow washing water divided by the screen underflow washing water dividing pipe 5 can be intelligently controlled by means of providing an electromagnetic flowmeter and an electromagnetic valve in the screen underflow washing water dividing pipe 5, that is, the valve mounted on the screen underflow washing water dividing pipe 5 is an electromagnetic valve, a controller is provided and electrically connected to the electromagnetic valve, and the opening degree of the electromagnetic valve is controlled by the controller according to the dry substance concentration of the fiber slurry in the external enzyme reaction tank 4, thereby realizing the intelligent control over the proportion of the screen underflow washing water divided by the screen underflow washing water dividing pipe 5. For example, when the dry substance concentration of the fiber slurry in the external enzyme reaction tank 4 is lower than 4%-6%, the opening degree of the electromagnetic valve is increased; and when the dry substance concentration of the fiber slurry in the external enzyme reaction tank 4 is higher than 4%-6% and the viscosity of the fiber slurry is too high, the opening degree of the electromagnetic valve is decreased. The electromagnetic valve is, for example, a pneumatic flow regulating valve, the pneumatic flow regulating valve is, for example, a Siemens VVF43 pneumatic flow regulating valve, and the electromagnetic flowmeter is, for example, a Siemens SITRANS F M MAG1100 electromagnetic flowmeter.

Embodiment 5

Figure 8:
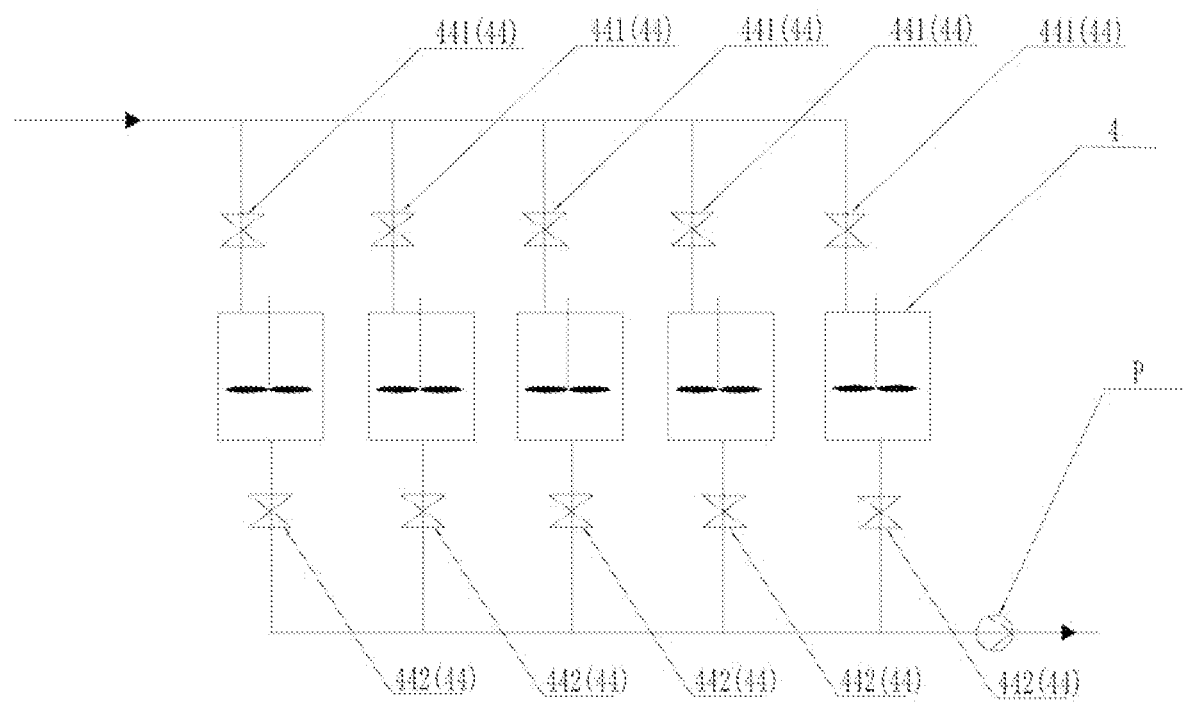
FIG. 8 is a structural schematic diagram of an external enzyme reaction tank provided in a particular embodiment of the present application.

In the maize fiber processing system in Embodiment 1 and Embodiment 2 of the present application, the external enzyme reaction tanks 4 may be batch reaction tanks. As shown in FIG. 8, at least three external enzyme reaction tanks 4 are provided, and the fiber slurry is controlled by valves 44 to simultaneously carry out feeding, enzyme reaction and discharging in the external enzyme reaction tank 4, that is, at the same time, only one reaction tank carries out feeding, only one reaction tank carries out discharging, and at least one reaction tank carries out an enzyme reaction. The valves 44 include first valves 441 and second valves 442. The feeding pipe of each reaction tank is provided with a first valve 441, and a discharge pipe of each reaction tank is provided with a second valve 442. At any time, only one first valve 441 and one second valve 442 are opened, and the opened first valve 441 and second valve 442 do not belong to the same reaction tank. In order to prevent the fiber slurry from precipitating in the reaction tank, each reaction tank is internally provided with a stirring device. When the second valve 442 is opened, in order to promote smooth discharge of the fiber slurry from the reaction tank, the returning pipe 41 may be provided with a pump P.

Embodiment 6

Figure 9:
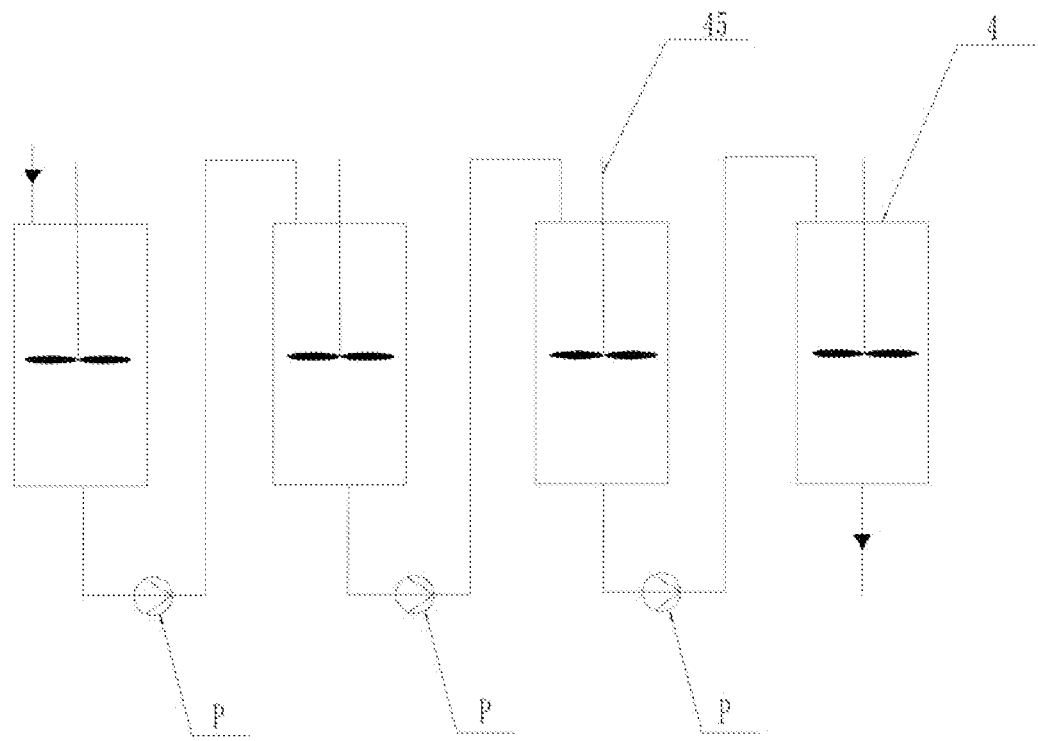
FIG. 9 is a structural schematic diagram of an external enzyme reaction tank provided in a particular embodiment of the present application.

In the maize fiber processing system in Embodiment 1 and Embodiment 2 of the present application, the external enzyme reaction tanks 4 may be continuous reaction tanks. As shown in FIG. 9, the external enzyme reaction tanks 4 include multiple reaction tanks, the multiple reaction tanks are connected in series, and each of the reaction tanks is internally provided with a first stirring device 45. The fiber slurry enters from the top end of each reaction tank and flows out from the bottom end of each reaction tank. In order to allow the fiber slurry to better flow in the reaction tank, sometimes a pump P is provided near the bottom end of each reaction tank to promote the flowing of the fiber slurry in the reaction tank.

Embodiment 7

Figure 10:
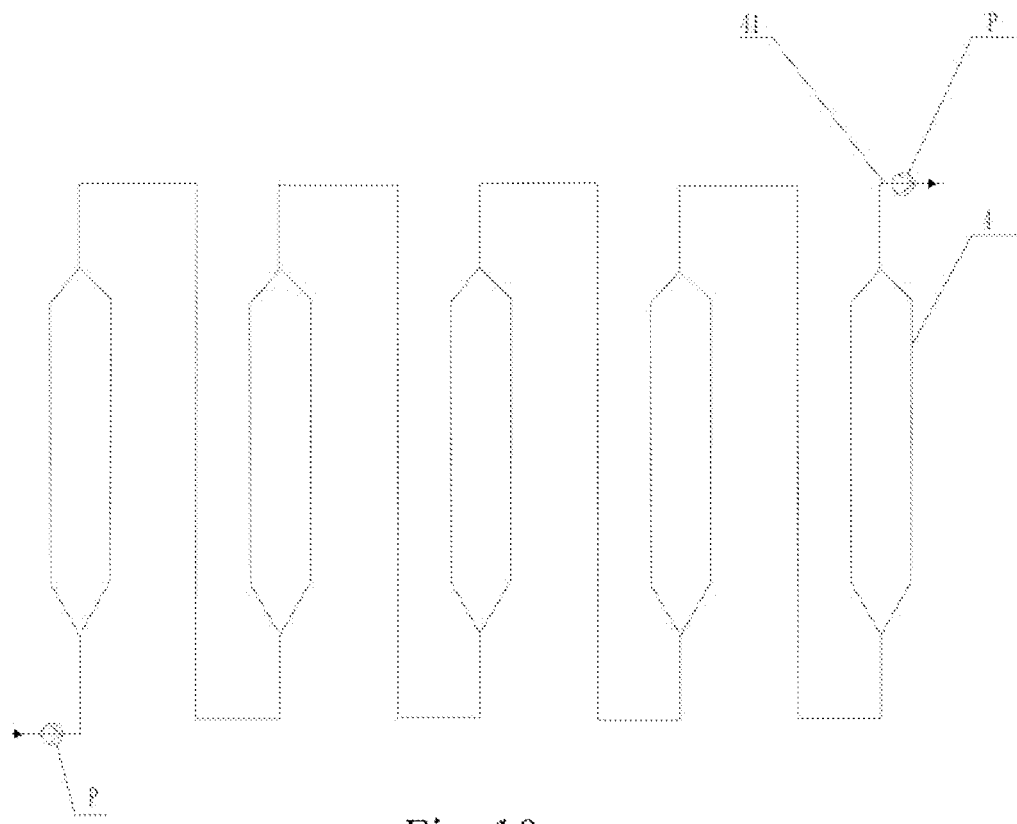
FIG. 10 is a structural schematic diagram of an external enzyme reaction tank provided in a particular embodiment of the present application.

In the maize fiber processing system in Embodiment 1 and Embodiment 2 of the present application, the external enzyme reaction tanks 4 may be continuous reaction tanks. As shown in FIG. 10, the external enzyme reaction tanks 4 include multiple reaction tanks, the multiple reaction tanks are connected in series, the fiber slurry enters from the bottom end of each reaction tank and flows out of the top end of each reaction tank, and the fiber slurry is transported to the reaction tank by the fiber washing sink 21, and the fiber slurry is pushed to flow in the reaction tanks under the action of the thrust from the subsequent fiber slurry. Compared with FIG. 9, no stirring device is provided in the external enzyme reaction tank 4, and the external enzyme reaction tank 4 has a diameter not greater than 1.2 meters. Such an external enzyme reaction tank 4 is also referred to as a laminar flow column, which can further save the cost. In order to allow the fiber slurry to better flow in the reaction tank, the input pipe and/or the returning pipe 41 of the external enzyme reaction tank 4 can be provided with a pump P to promote the flowing of the fiber slurry in the reaction tank.

Embodiment 8

Figure 11:
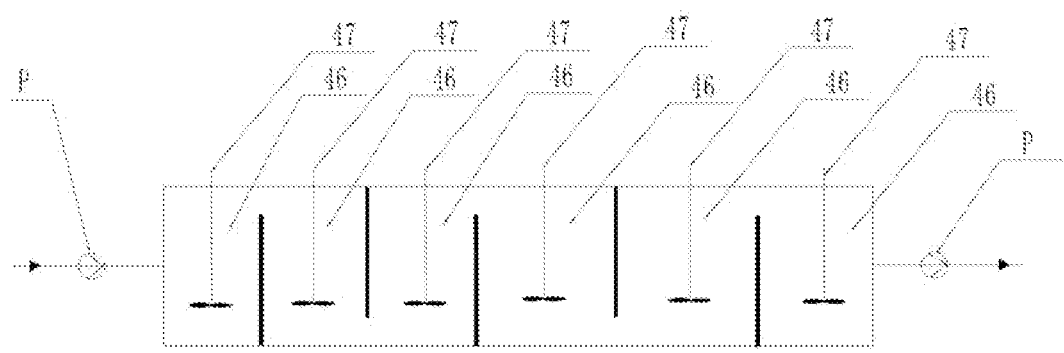
FIG. 11 is a structural schematic diagram of an external enzyme reaction tank provided in a particular embodiment of the present application.

With reference to FIG. 11, compared with the external enzyme reaction tanks 4 in Embodiment 6 and Embodiment 7, only one external enzyme reaction tank 4 is provided in Embodiment 8. The external enzyme reaction tank 4 is a horizontal enzyme reaction tank in form, which reduces the space occupation of the external enzyme reaction tank 4, and there are many compartments in the horizontal enzyme reaction tank. As shown in FIG. 11, the horizontal enzyme reaction tank has multiple horizontally arranged first compartments 46 and second stirring devices 47 corresponding to the first compartments 46, and the fiber slurry can sequentially flow through the first compartments 46. The flow path of the fiber slurry in the first compartment 47 is sinusoidal, linear or S-shaped as a whole. In order to allow the fiber slurry to smoothly flow in the external enzyme reaction tank 4, the input pipe and/or the returning pipe 41 of the external enzyme reaction tank 4 can be provided with a pump P to promote the flowing of fiber slurry.

Embodiment 9

Figure 12:
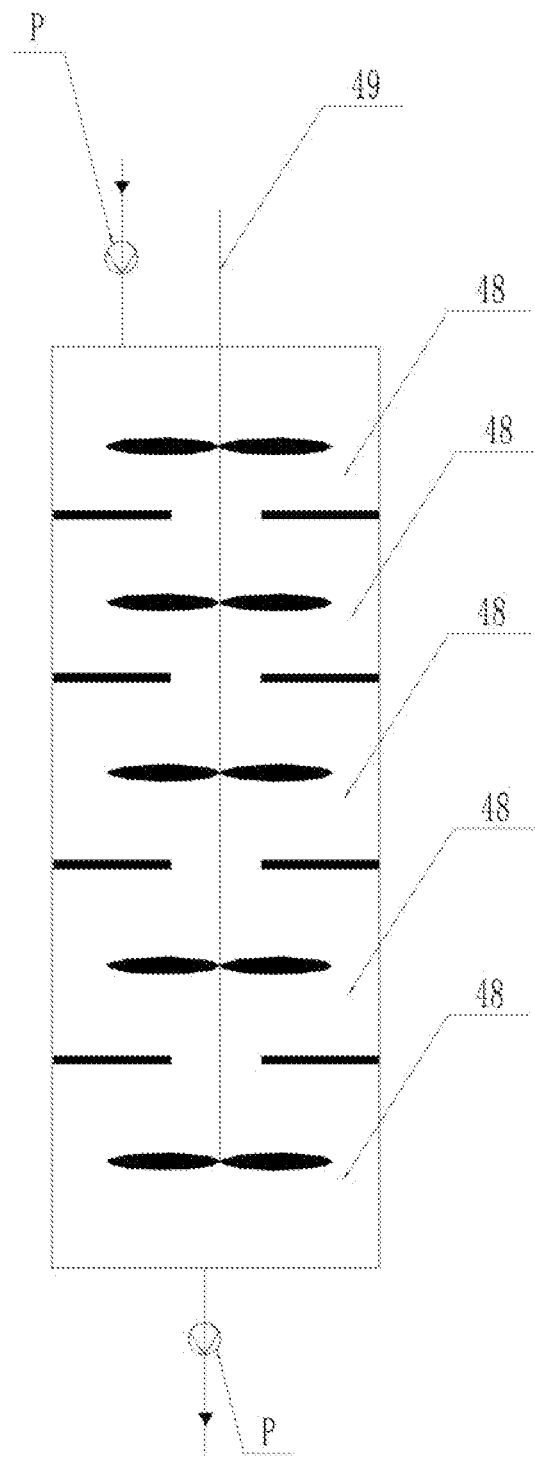
FIG. 12 is a structural schematic diagram of an external enzyme reaction tank provided in a particular embodiment of the present application.

In the maize fiber processing system in Embodiment 1 and Embodiment 2 of the present application, the external enzyme reaction tank 4 may be a vertical enzyme reaction tank. As shown in FIG. 12, the vertical enzyme reaction tank has multiple vertically arranged second compartments 48 and third stirring devices 49 corresponding to the second compartments 48, and the fiber slurry can sequentially flow through the second compartments 48. The third stirring device has multiple vertically arranged stirring blades which correspond to the second compartments on a one-to-one basis, with the second compartments being in communication in sequence, and the stirring blade stirs the fiber slurry in the corresponding second compartment. In order to allow the fiber slurry to smoothly flow in the external enzyme reaction tank 4, the input pipe and/or the returning pipe 41 of the external enzyme reaction tank 4 can be provided with a pump P to promote the flowing of fiber slurry.

Embodiment 10

Figure 13:
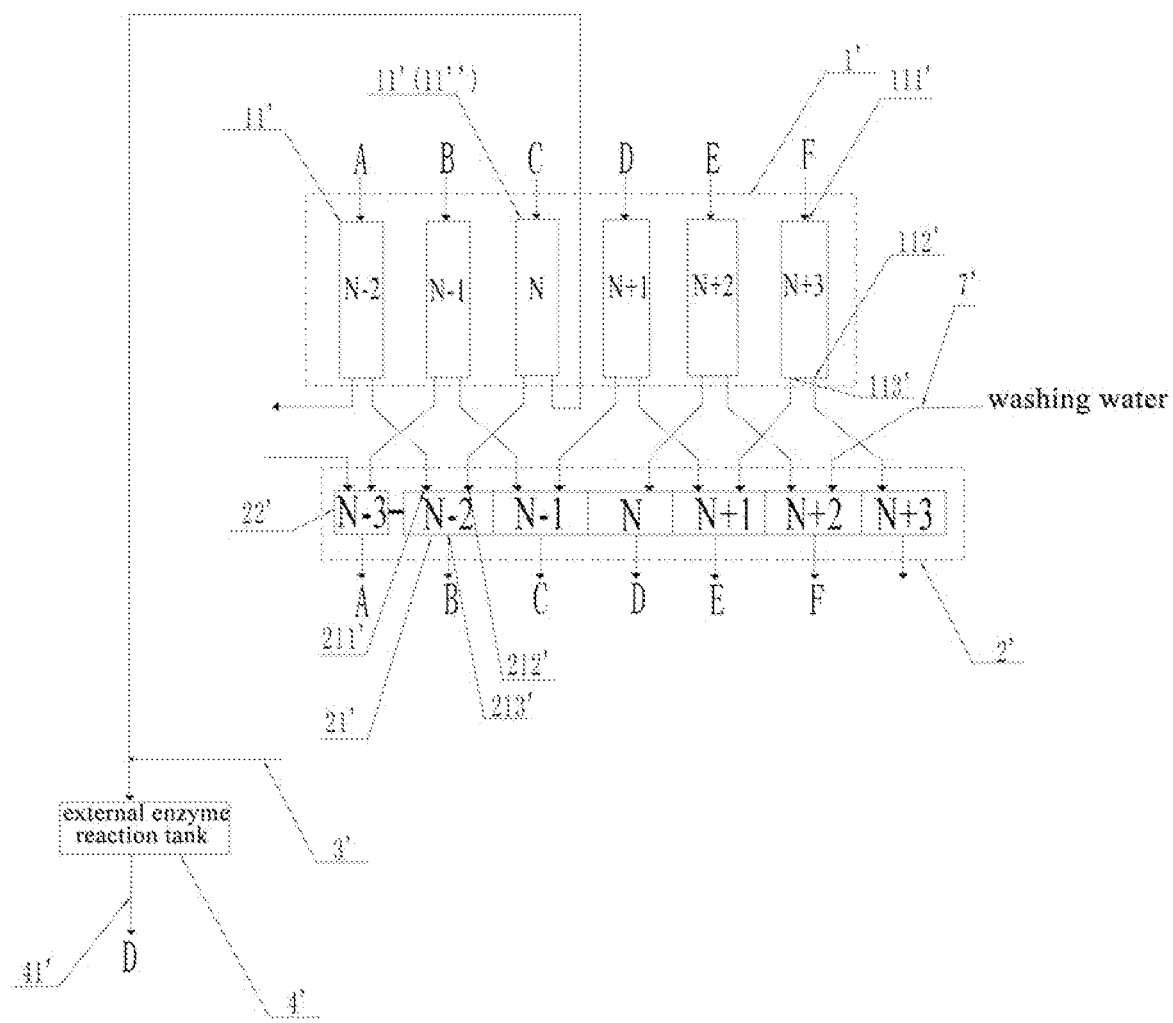
FIG. 13 is a structural schematic diagram of a maize fiber processing system for extracting maize starch provided in a particular embodiment of the present application.

With reference to FIG. 13, a maize fiber processing system for extracting maize starch may comprise: a pressure curved screen group 1', a fiber washing sink group 2', an enzyme preparation adding device 3' and an external enzyme reaction tank 4'. The pressure curved screen group 1' matches the fiber washing sink group 2'.

The pressure curved screen group 1' has multiple stages of pressure curved screens 11', the pressure curved screens 11' are used for separating fiber slurry containing starch and protein into screen overflow (screen overflow fiber) and screen underflow (screen underflow washing water), and each stage of the pressure curved screen 11' has a fiber slurry inlet 111', a screen overflow outlet 112' and a screen underflow outlet 113'. For ease of description, it is assumed that the pressure curved screen group 1 has six stages of pressure curved screens 11', including a pressure curved screen N−2 (the leftmost end of pressure curved screen), a pressure curved screen N−1 (a middle stage of pressure curved screen), a pressure curved screen N (a middle stage of pressure curved screen), a pressure curved screen N+1 (a middle stage of pressure curved screen), a pressure curved screen N+2 (a middle stage of pressure curved screen), and a pressure curved screen N+3 (the rightmost end of pressure curved screen).

In the embodiment of the present application, except for the leftmost end of pressure curved screen and the rightmost end of pressure curved screen, the remaining pressure curved screens may be referred to as the middle stage of pressure curved screens, or only the pressure curved screen N is referred to as the middle stage of pressure curved screen. The screen overflow mainly comprises wet fiber, attached starch and protein, etc., and the screen underflow mainly comprises screen underflow washing water, starch, protein, etc. A first stage of screen underflow (screen underflow output from a screen underflow outlet 113' of the pressure curved screen N−2) is crude starch milk, a second stage of screen underflow (screen underflow output from a screen underflow outlet 113' of the pressure curved screen N−1) comes from screen underflow separated from the previous stage of pressure curved screen (the pressure curved screen N), and starch milk concentration is getting lower and lower. Preferably, the middle stage of pressure curved screen refers to any stage of pressure curved screen other than the first stage of pressure curved screen and the last stage of pressure curved screen in the pressure curved screen group. More preferably, the middle stage of pressure curved screen refers to the pressure curved screen in a middle position, that is, referring to the pressure curved screen in the middle position if there are odd-numbered pressure curved screens, or referring to the first pressure curved screen in the middle position if there are even-numbered pressure curved screens. As shown in FIG. 13, the middle stage of pressure curved screen refers to the pressure curved screen N.

Further, screen underflow of the corresponding first stage of pressure curved screen 11' flows to a gluten separating system, and the screen underflow of the corresponding second stage of pressure curved screen 11' flows to a material supply buffer tank 22' of a maize fiber system.

In a particular embodiment of the present application, the pressure curved screen 11' is used for separating the fiber slurry containing starch and protein into the screen overflow and the screen underflow, the screen overflow of the pressure curved screen 11' flows to the corresponding stage of fiber washing sink 21' among the fiber washing sink group 2' through the screen overflow outlet 112', and the screen underflow of the pressure curved screen 11' flows to the fiber washing sink 21' before the corresponding stage of fiber washing sink 21' among the fiber washing sink group 2' through the screen underflow outlet 113'. For example, the fiber washing sink 21' connected to the screen overflow outlet 112' of the pressure curved screen 11' is not adjacent to, preferably one stage of fiber washing sinks 21' apart from, the fiber washing sink 21' connected to the screen underflow outlet 113' of the pressure curved screen 11. In a preferred embodiment of the present application, the screen underflow of the pressure curved screen 11' flows to a small material compartment of the fiber washing sink 21' which is supplied with the material by the pressure curved screen among the fiber washing sink group 2' through the screen underflow outlet 113', and overflows to the previous fiber washing sink 21' through the small material compartment.

In a preferred embodiment of the present application, the fiber washing sink 21' connected to the screen overflow outlet 112' of the pressure curved screen 11' is one stage of fiber washing sink 21' apart from the fiber washing sink 21' connected to the screen underflow outlet 113 of the pressure curved screen 11'. As shown in FIG. 13, the pressure curved screen N−2 supplies the screen overflow fiber (the screen overflow) to the fiber washing sink N−2, and supplies the screen underflow washing water to the gluten separating system later. The pressure curved screen N−1 supplies the screen overflow fiber to the fiber washing sink N−1, and supplies the screen underflow washing water to the front-placed washing sink N−3 (i.e., the material supply buffer tank) later. The pressure curved screen N supplies the screen overflow fiber to the fiber washing sink N, and supplies the screen underflow washing water to the fiber washing sink N−2 later. The pressure curved screen N+1 supplies the screen overflow fiber to the fiber washing sink N+1, and supplies the screen underflow washing water to the fiber washing sink N−1 later. The pressure curved screen N+2 supplies the screen overflow fiber to the fiber washing sink N+2, and supplies the screen underflow washing water to the fiber washing sink N later. The pressure curved screen N+3 supplies the screen overflow fiber to the fiber washing sink N+3, and supplies the screen underflow washing water to the fiber washing sink N+1 later. In a more preferred embodiment of the present application, the pressure curved screen N−2 supplies the screen overflow fiber to the fiber washing sink N−2, and supplies the screen underflow washing water to the gluten separating system later. The pressure curved screen N−1 supplies the screen overflow fiber to the fiber washing sink N−1, and supplies the screen underflow washing water to the front-placed washing sink N−3 (i.e., the material supply buffer tank) later. The pressure curved screen N supplies the screen overflow fiber to the fiber washing sink N, and supplies the screen underflow washing water to the small material compartment of the fiber washing sink N−1, which overflows into the fiber washing sink N−2 through the small material compartment of the fiber washing sink N−1. The pressure curved screen N+1 supplies the screen overflow fiber to the fiber washing sink N+1, and supplies the screen underflow washing water to the small material compartment of the fiber washing sink N later, which overflows into the fiber washing sink N−1 through the small material compartment of the fiber washing sink N. The pressure curved screen N+2 supplies the screen overflow fiber to the fiber washing sink N+2, and supplies the screen underflow washing water to the small material compartment of the fiber washing sink N+1 later, which overflows into the fiber washing sink N through the small material compartment of the fiber washing sink N+1. The pressure curved screen N+3 supplies the screen overflow fiber to the fiber washing sink N+3, and supplies the screen underflow washing water to the small material compartment of the fiber washing sink N+2, which overflows into the fiber washing sink N+1 through the small material compartment of the fiber washing sink N+2, which is not limited thereof in the present application.

The above is merely one embodiment of the present application, and the pressure curved screen group 1' and the fiber washing sink group 2' may also match in the way as follows: The pressure curved screen N−2 supplies the screen overflow fiber to the fiber washing sink N−2, and supplies the screen underflow washing water to the gluten separating system later. The pressure curved screen N−1 supplies the screen overflow fiber to the fiber washing sink N−1, and supplies the screen underflow washing water to the gluten separating system later. The pressure curved screen N supplies the screen overflow fiber to the fiber washing sink N, and supplies the screen underflow washing water to the front-placed washing sink N−3 later. The pressure curved screen N+1 supplies the screen overflow fiber to the fiber washing sink N+1, and supplies the screen underflow washing water to the fiber washing sink N−2 later. The pressure curved screen N+2 supplies the screen overflow fiber to the fiber washing sink N+2, and supplies the screen underflow washing water to the fiber washing sink N−1 later. The pressure curved screen N+3 supplies the screen overflow fiber to the fiber washing sink N+3, and supplies the screen underflow washing water to the fiber washing sink N later, which are not limited thereto in the present application.

The fiber washing sink group 2' is used for providing a place for washing the fiber slurry by washing water, the fiber washing sink group 2' has multiple stages of fiber washing sinks 21', and each stage of the fiber washing sink 21' has a screen overflow feeding port 211', a screen underflow feeding port 212' and a discharge port 213'. In the same way, for ease of description, it is assumed that the fiber washing sink group 2' has six stages of fiber washing sinks 21', including the fiber washing sink N−2, the fiber washing sink N−1, the fiber washing sink N, the fiber washing sink N+1, the fiber washing sink N+2, and fiber washing sinks N+3. Preferably, the middle stage of fiber washing sink refers to any stage of fiber washing sink other than the first stage of fiber washing sink and the last stage of fiber washing sink among the middle stage of fiber washing sink group, that is, any remaining fiber washing sink other than the fiber washing sink N−2 and the fiber washing sink N+3. More preferably, the middle stage of fiber washing sink refers to a fiber washing sink in a middle position. If there are odd-numbered fiber washing sinks, the middle stage of fiber washing sink refers to the fiber washing sink in the middle position; and if there are even-numbered fiber washing sinks, the middle stage of fiber washing sink refers to the first fiber washing sink in the middle position, for example, the middle stage of fiber washing sink refers to the fiber washing sink N.

Further, for the temporarily storage of the fiber slurry and the better control of the fiber washing process, the front end of the fiber washing sink N−2 can be further provided with a front-placed washing sink N−3. The front-placed washing sink N−3 is also referred to as the material supply buffer tank 22', and receives the screen underflow of the corresponding second stage of pressure curved screen 11 (i.e., the pressure curved screen N−1) and the fiber material produced by a fine milling system, and the screen underflow and the fiber material are thoroughly mixed in the material supply buffer tank 22 to form the fiber slurry. In order to realize countercurrent washing of maize fiber, the pressure curved screen group 1' and the fiber washing sink group 2' are arranged cooperatively, the fiber slurry output from the discharge port 213' of the fiber washing sink 21' is transported to the next stage of pressure curved screen 11', the screen overflow fiber output from the screen overflow outlet 112 of the pressure curved screen 11 is transported to the corresponding fiber washing sink 21', the screen underflow washing water output from the screen underflow outlet 113 of the pressure curved screen 11 is transported to two higher stages of fiber washing sinks 21', thus realizing the movement of the fiber dry substance from a lower stage of fiber washing sink 21' to a higher stage of fiber washing sink 21', and the movement of the screen underflow washing water from the higher stage of fiber washing sink 21' to the lower stage of fiber washing sink 21', thereby realizing countercurrent washing of maize fiber. For example, the fiber slurry output from the discharge port 213' of the fiber washing sink N+2 is transported to the pressure curved screen N+3, the screen overflow fiber output from the screen overflow outlet 112 of pressure curved screen N+3 is transported to the fiber washing sink N+3, and the screen underflow washing water output from the screen underflow outlet 113 of the pressure curved screen N+3 is transported to the fiber washing sink N+1.

The enzyme preparation adding device 3' is used for adding the enzyme preparation into the maize fiber processing system. The enzyme preparation reacts with the fiber slurry, such that the fiber slurry releases more free starch, bound starch and maize protein. The enzyme preparation adding device 3' may be an enzyme preparation adding pipe, and the enzyme preparation adding pipe 3' may be connected to an input pipe of the external enzyme reaction tank 4', as shown in FIG. 13. In addition, the enzyme preparation adding pipe 3' may also be connected to the screen overflow outlet 112' of the middle stage of pressure curved screen 11", and the enzyme preparation adding pipe 3' may also be connected to the external enzyme reaction tank 4'. The enzyme preparation can be manually added through the enzyme preparation adding pipe 3', and can also be added through the enzyme preparation adding pipe 3' by means of a pump, which is not limited thereto in the present application.

The external enzyme reaction tank 4' is connected to the screen overflow outlet 112' of the middle stage of pressure curved screen 11", the external enzyme reaction tank 4' is used for receiving the screen overflow in the middle stage of pressure curved screen 11" and providing a place for enzyme reaction, the screen overflow in the external enzyme reaction tank 4' is returned back to the fiber slurry inlet 111' of the next stage of pressure curved screen 11' posterior to the middle stage of pressure curved screen 11" through the returning pipe 41' after predetermined time. According to the requirements for equipment space and fiber slurry retention time, the external enzyme reaction tank 4' may be one tank or a combined tank formed of multiple tanks. The specific form of the external enzyme reaction tank 4' will be illustrated in the following embodiments, which will not be repeated herein in view of the length. As shown in FIG. 13, it is assumed that the fiber washing sink group 2' has six stages of fiber washing sinks 21', the pressure curved screen group 1' has six stages of pressure curved screens 11', the middle stage of fiber washing sink is the fiber washing sink N, the middle stage of pressure curved screen 11" is the pressure curved screen N, and the next stage of pressure curved screen 11' posterior to the middle stage of pressure curved screen 11" is the pressure curved screen N+1.

The pressure curved screen group 1' is usually located at a very high position, and the screen overflow of the middle stage of pressure curved screen 11" automatically flows into the external enzyme reaction tank 4' under the action of its own gravity, without the need for an external pump. In addition, in order to allow the screen overflow to smoothly flow in the external enzyme reaction tank 4', the pump can be provided at the returning pipe 41' of the external enzyme reaction tank 4', such that the screen overflow or diluted screen overflow output from the external enzyme reaction tank 4' is returned back to the fiber slurry inlet 111' of the next stage of pressure curved screen 11' to promote the flowing of the fiber slurry. In addition, the screen overflow output from the middle stage of pressure curved screen 11" will stay in the external enzyme reaction tank 4' for a period of time, such that the external enzyme reaction tank 4' extends the reaction time of the enzyme preparation to further improve the yield of maize starch and/or maize protein.

Embodiment 11

Figure 14:
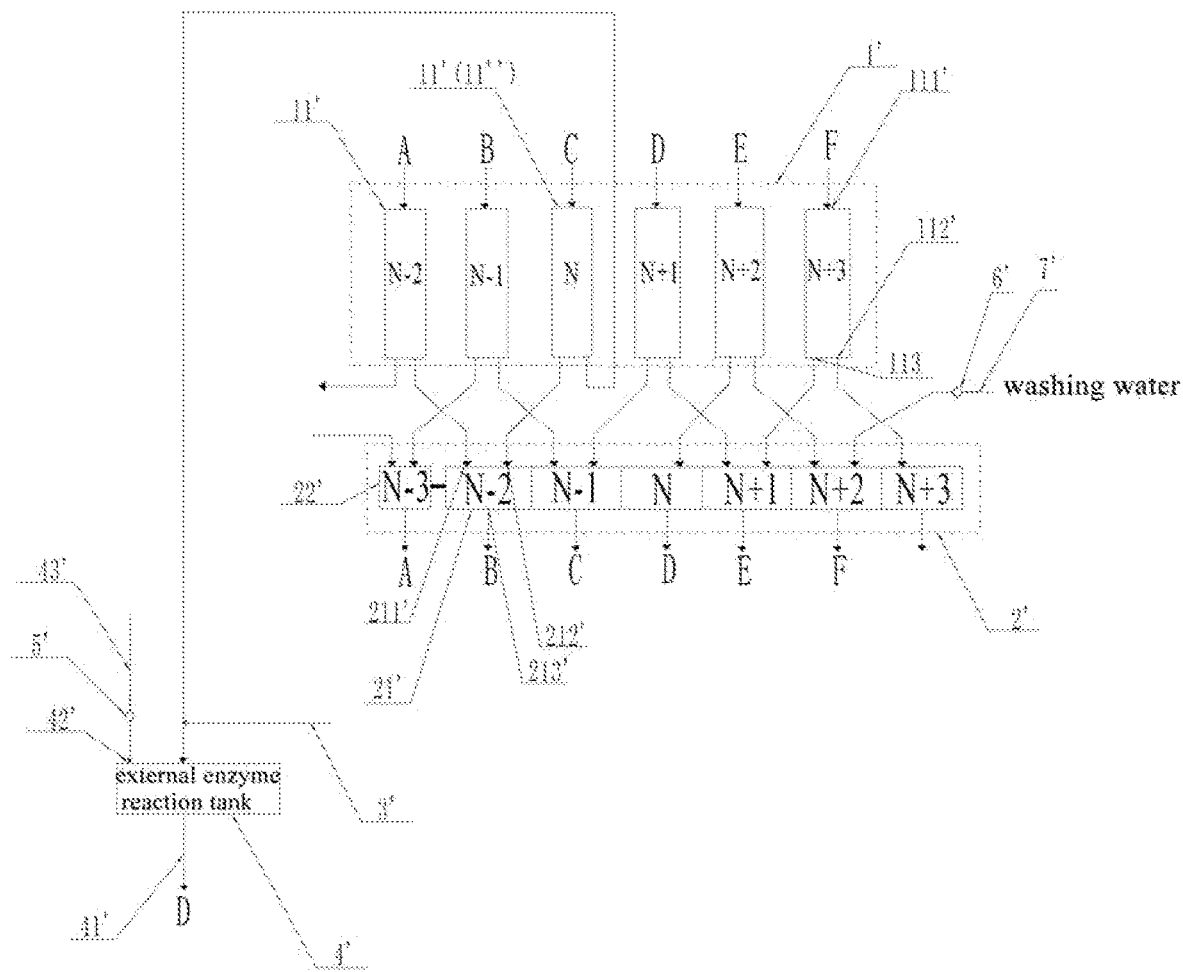
FIG. 14 is a structural schematic diagram of a maize fiber processing system for extracting maize starch provided in a particular embodiment of the present application.

With reference to FIG. 14, the fiber dry substance concentration of screen overflow fiber may affect the performance of enzyme preparation, and in order to achieve a better performance of the enzyme preparation, the fiber dry substance concentration should be 4%-6% (with the non-fiber dry substance in the fiber slurry being washed off with a 75 micron screen). A lower fiber dry substance concentration may lead to a lower enzyme preparation performance, but the fiber dry substance concentration of the screen overflow output from the middle stage of pressure curved screen 11" is generally 7%-8%, and too high fiber dry substance concentration is not conducive to the flowing of the screen overflow in an external enzyme reaction tank 4'; therefore, controlling the fiber dry substance concentration of the screen overflow is conducive to promoting the flowing of the screen overflow in the external enzyme reaction tank 4'. According to the above description of Embodiment 1, the external enzyme reaction tank 4' has an injecting water inlet 42' for adjusting the fiber dry substance concentration of the screen overflow in the external enzyme reaction tank 4', and the washing water can be injected through the injecting water inlet 42', such that the fiber dry substance concentration of the screen overflow in the external enzyme reaction tank 4' is 4%-6%, the screen overflow diluted by the washing water (i.e., the diluted screen overflow) smoothly flows in the external enzyme reaction tank 4', and the enzyme preparation achieves a better performance.

In a preferred embodiment of the present application, the injecting water inlet 42' is externally connected to a injecting water pipe 43' for adjusting the fiber dry substance concentration of the screen overflow in the external enzyme reaction tank 4', and the injecting water pipe 43' is directly connected to washing water outside a maize fiber processing system to dilute the fiber dry substance concentration of the screen overflow in the external enzyme reaction tank 4' from 7%-8% to 4%-6%, such that the screen overflow diluted by the washing water smoothly flows in the external enzyme reaction tank 4', and the enzyme preparation achieves a better performance.

More preferably, a first flow controlling device 5' is provided near the injecting water inlet 42' to control the amount of washing water injected into the external enzyme reaction tank 4' to dilute the fiber dry substance concentration of the screen overflow in the external enzyme reaction tank 4' from 7%-8% to 4%-6%, such that the screen overflow diluted by the washing water smoothly flows in the external enzyme reaction tank 4', and the enzyme preparation achieves a better performance. Since injecting the washing water into the external enzyme reaction tank 4' will change the total amount of water in the maize fiber processing system, it is necessary to correspondingly reduce the amount of washing water injected into the maize fiber processing system according to the amount of injecting water received by the external enzyme reaction tank 4', that is, to correspondingly reduce the amount of washing water injected into the maize fiber processing system according to the amount of injecting water, so as to keep the total amount of water (the total amount of washing water) of the maize fiber processing system unchanged.

With reference to FIG. 14 again, in a preferred embodiment of the present application, the second flow controlling device 6' is provided near the washing water inlet 7' of the maize fiber processing system, and is used for controlling the water inflow amount of external washing water of the maize fiber processing system. Preferably, the amount of washing water injected into the external enzyme reaction tank 4' is equal to the amount of washing water injected from the washing water inlet 7', so as to keep the total amount of water in the maize fiber processing system unchanged and keep the fiber dry substance concentration of the whole fiber slurry in the fiber washing sink 21' in an original maize fiber processing system unchanged.

In a particular embodiment of the present application, the first flow controlling device 5' and the second flow controlling device 6' may be flow meters, flow valves, electromagnetic flow valves, etc. The first flow controlling device 5' and the second flow controlling device 6' can be manually operated by a worker, such that the amount of washing water injected into the external enzyme reaction tank 4' is equal to the reduced amount of washing water injected into the washing water inlet 7'. The automatic control may also be achieved. For example, a processor is provided and is simultaneously connected to both the first flow controlling device 5' and the second flow controlling device 6'. The processor obtains the amount of washing water injected into the external enzyme reaction tank 4' from the first flow controlling device 5', controls the second flow controlling device 6' according to the amount of washing water injected into the external enzyme reaction tank 4', and reduces the amount of washing water injected through the washing water inlet 7'. The processor can use a digital signal processor (DSP), a single-chip microcomputer, an application specific integrated circuit (ASIC), a field programmable gate array (FPGA), a system on a chip (SoC), etc., which will not be repeated herein, because the processor is selected from common existing data processing components.

Embodiment 12

In the maize fiber processing system in Embodiment 10 and Embodiment 11 of the present application, the screen overflow from the middle stage of pressure curved screen 11" and the washing water from the injecting water inlet 42' of the external enzyme reaction tank 4' converge in the external enzyme reaction tank 4' to form the diluted screen overflow, which is evenly mixed to achieve relatively stable fiber dry substance concentration. The first flow controlling device 5' can be controlled according to the fiber dry substance concentration of the diluted screen overflow in the external enzyme reaction tank 4', so as to control the amount of washing water injected into the external enzyme reaction tank 4' to adjust the fiber dry substance concentration of the diluted screen overflow, such that the fiber dry substance concentration of the diluted screen overflow in the external enzyme reaction tank 4' is maintained at 4%-6%, and the enzyme preparation is in a better reaction state.

Further, a processor is used and is simultaneously electrically connected to the first flow controlling device 5' and the second flow controlling device 6'. The processor controls the opening degree of the first flow controlling device 5' according to the dry substance concentration of the diluted screen overflow in the external enzyme reaction tank 4', and controls injection of washing water into the external enzyme reaction tank 4', thereby realizing intelligent control over the fiber dry substance concentration of the diluted screen overflow in the external enzyme reaction tank 4'. For example, when the fiber dry substance concentration of the diluted screen overflow in the external enzyme reaction tank 4' is lower than 4%-6%, the opening degree of the first flow controlling device 5' is increased; and when the fiber dry substance concentration of the diluted screen overflow in the external enzyme reaction tank 4' is higher than 4%-6% and the viscosity of the diluted screen overflow is too high, the opening degree of the first flow controlling device 5' is decreased. The first flow controlling device 5' may use a pneumatic flow regulating valve or an electromagnetic flowmeter. The pneumatic flow regulating valve may be, for example, a Siemens VVF43 pneumatic flow regulating valve, and the electromagnetic flowmeter may be, for example, a Siemens SITRANS F M MAG1100 electromagnetic flowmeter. Further, the processor obtains the amount of washing water injected into the external enzyme reaction tank 4' from the first flow controlling device 5', and controls the second flow controlling device 6' according to the amount of washing water injected into the external enzyme reaction tank 4' to reduce the amount of washing water injected through a washing water inlet 7' to keep the total amount of water (the total amount of washing water) of the maize fiber processing system unchanged. The second flow controlling device 6' may use a pneumatic flow regulating valve or an electromagnetic flowmeter. The pneumatic flow regulating valve may be, for example, a Siemens VVF43 pneumatic flow regulating valve, and the electromagnetic flowmeter may be, for example, a Siemens SITRANS F M MAG1100 electromagnetic flowmeter.

Embodiment 13

Figure 15:
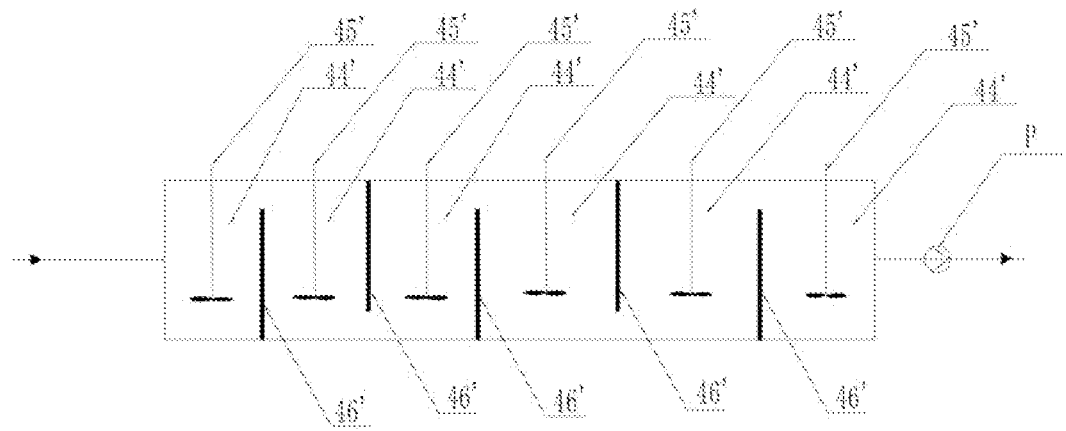
FIG. 15 is a structural schematic diagram of an external enzyme reaction tank provided in a particular embodiment of the present application.

In the maize fiber processing systems in Embodiment 10 and Embodiment 11 of the present application, only one external enzyme reaction tank 4' may be provided. As shown in FIG. 15, the external enzyme reaction tank 4' is a horizontal enzyme reaction tank in form, which reduces space occupation of the external enzyme reaction tank 4', and there are many compartments in the horizontal enzyme reaction tank. As shown in FIG. 15, the horizontal enzyme reaction tank has multiple horizontally arranged first compartments 44' and first stirring devices 45' corresponding to the first compartments 44', and the fiber slurry may sequentially flows through the first compartments 44'.

Preferably, the horizontal enzyme reaction tank has multiple vertically and alternately arranged semi-closed isolation plates 46', which are used for dividing the horizontal enzyme reaction tank into multiple first compartments 44'. The flow path of the diluted screen overflow in the multiple first compartments 44' are sinusoidal or S-shaped as a whole, such that the diluted screen overflow may be thoroughly stirred to improve the reaction efficiency of the enzyme preparation. In order to allow the diluted screen overflow to smoothly flow in the horizontal enzyme reaction tank, the returning pipe 41' of the horizontal enzyme reaction tank can be provided with a pump P to promote the flowing of the diluted screen overflow.

Embodiment 14

Figure 16:
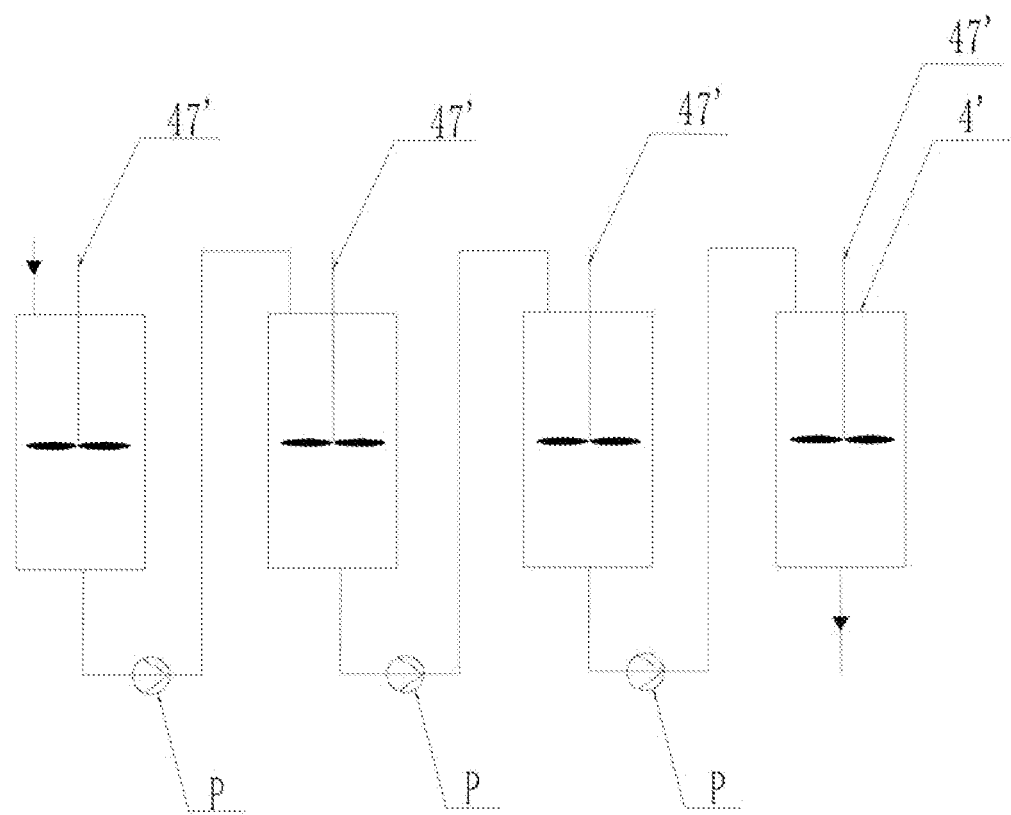
FIG. 16 is a structural schematic diagram of an external enzyme reaction tank provided in a particular embodiment of the present application.

In the maize fiber processing system in Embodiment 10 and Embodiment 11 of the present application, the external enzyme reaction tanks 4' may be continuous reaction tanks. As shown in FIG. 16, the external enzyme reaction tanks 4' include multiple reaction tanks, which are connected in series, and each of which is provided with a second stirring device 47'. The diluted screen overflow enters from the top end of each reaction tank and flows out from the bottom end of each reaction tank (also referred to as a top-entry reaction tank), and in order to allow the diluted screen overflow to better flow in the reaction tank, sometimes a pump P is provided near the bottom end of each reaction tank to promote the continuous flowing of the diluted screen overflow in the reaction tank.

Embodiment 15

Figure 17:
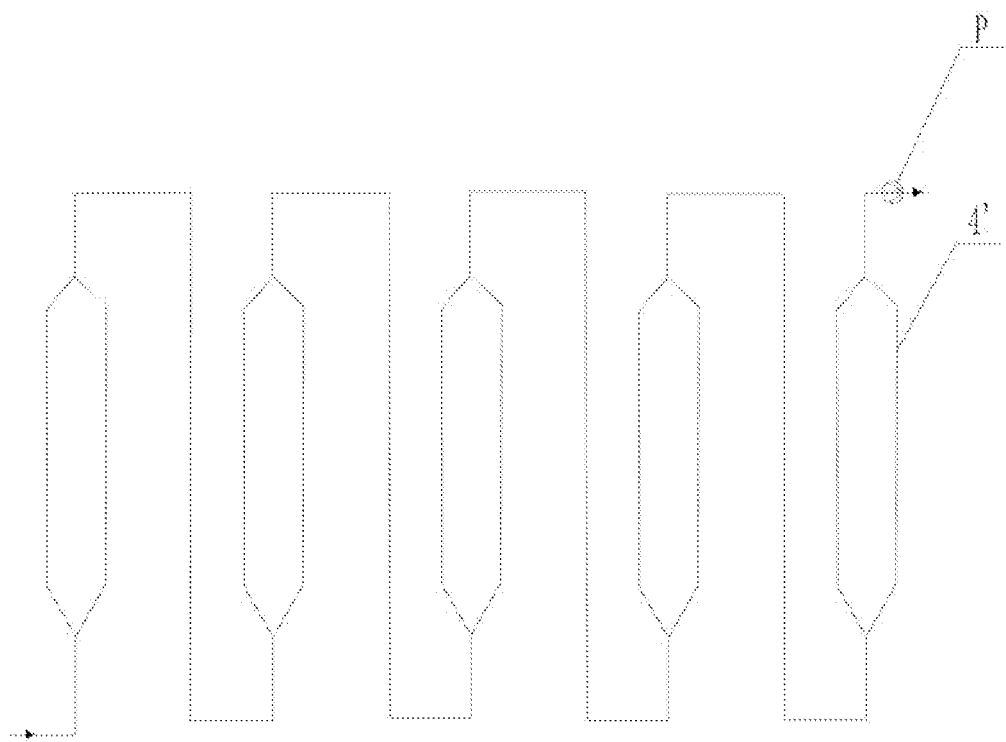
FIG. 17 is a structural schematic diagram of an external enzyme reaction tank provided in a particular embodiment of the present application.

In the maize fiber processing system in Embodiment 10 and Embodiment 11 of the present application, the external enzyme reaction tank 4' may be continuous reaction tanks. As shown in FIG. 17, the external enzyme reaction tanks 4' include multiple reaction tanks which are connected in series, the diluted screen overflow enters from the bottom end of each reaction tank (also referred to as a bottom-entry reaction tank) and flows out from the top end of each reaction tank, the diluted screen overflow is transported by the middle stage of pressure curved screen 11" to the reaction tank, and the diluted screen overflow is pushed to continuously flow in the reaction tank under the action of the thrust from the subsequent diluted screen overflow. Compared with FIG. 16, no stirring device is provided in the external enzyme reaction tank 4', each reaction tank has a diameter not greater than 1.2 meters, and such an external enzyme reaction tank 4' is referred to as a laminar flow column as well, such that the cost is further saved. In order to allow the diluted screen overflow in the external enzyme reaction tank 4' to finally smoothly flow back to the fiber slurry inlet 111' of the next stage of pressure curved screen 11 posterior to the middle stage of pressure curved screen 11", the returning pipe 41' of the external enzyme reaction tank 4' can be provided with a pump P, and the pump P provided can simultaneously promote the sequential flowing of the diluted screen overflow in the multiple reaction tanks connected in series.

Embodiment 16

Figure 18:
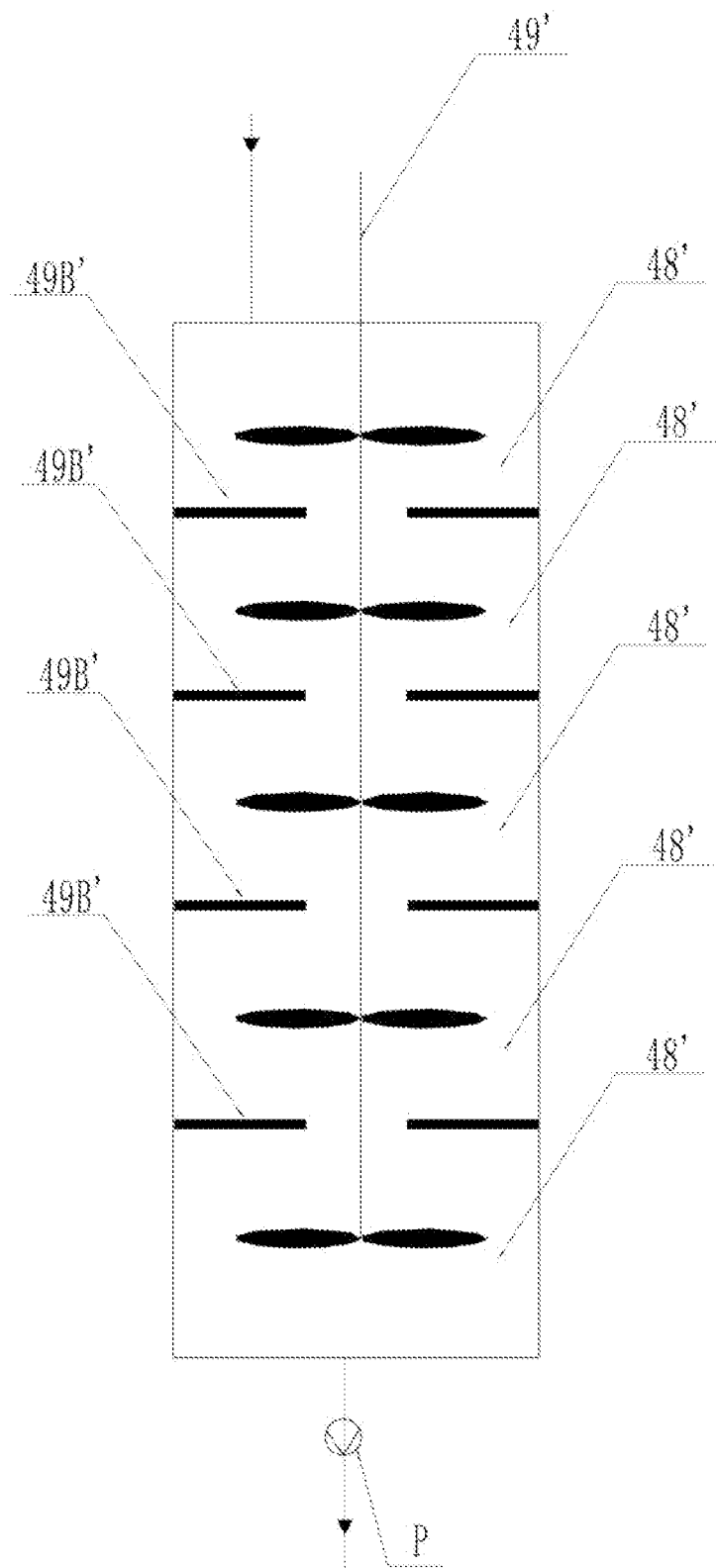
FIG. 18 is a structural schematic diagram of an external enzyme reaction tank provided in a particular embodiment of the present application.

In the maize fiber processing system in Embodiment 10 and Embodiment 11 of the present application, the external enzyme reaction tank 4' may be a vertical enzyme reaction tank. As shown in FIG. 18, the vertical enzyme reaction tank has multiple vertically arranged second compartments 48' and third stirring devices 49' corresponding to the second compartments 48', and the fiber slurry can sequentially flow through the second compartments 48'. The third stirring device 49' has multiple vertically arranged stirring blades which correspond to the second compartments on a one-to-one basis, with the second compartments being in communication in sequence, and the stirring blade stirs the fiber slurry in the corresponding second compartment. In order to allow the diluted screen overflow in the external enzyme reaction tank 4' to finally smoothly flow back to the fiber slurry inlet 111' of the next stage of pressure curved screen 11' posterior to a middle stage of pressure curved screen 11", the returning pipe 41' of the external enzyme reaction tank 4' can be provided with a pump P.

In a preferred embodiment of the present application, the vertical enzyme reaction tank has multiple vertically arranged baffles 49B' which are hollowed in the middle. If the vertical enzyme reaction tank is cylindrical, the baffle 49B' is ring-shaped; and if the vertical enzyme reaction tank is in a square column shape, the baffle 49B' is in a concentric-square shape. The baffles 49B' are used for dividing the vertical enzyme reaction tank into multiple vertically distributed second compartments 48'. Due to presence of the baffle 49B', the third stirring device 49' can thoroughly stir the diluted screen overflow so as to improve the reaction efficiency of enzyme preparation.

Further, the volume of the external enzyme reaction tank 4' and the flow of the fiber slurry are determined by the daily maize processing capacity of the maize wet-milled starch processing system, for example, for the maize wet-milled starch processing system with the daily processing capacity of 1500 tons of maize, the volume of the external enzyme reaction tank 4' is 300 m$^3$.

Figure 19:
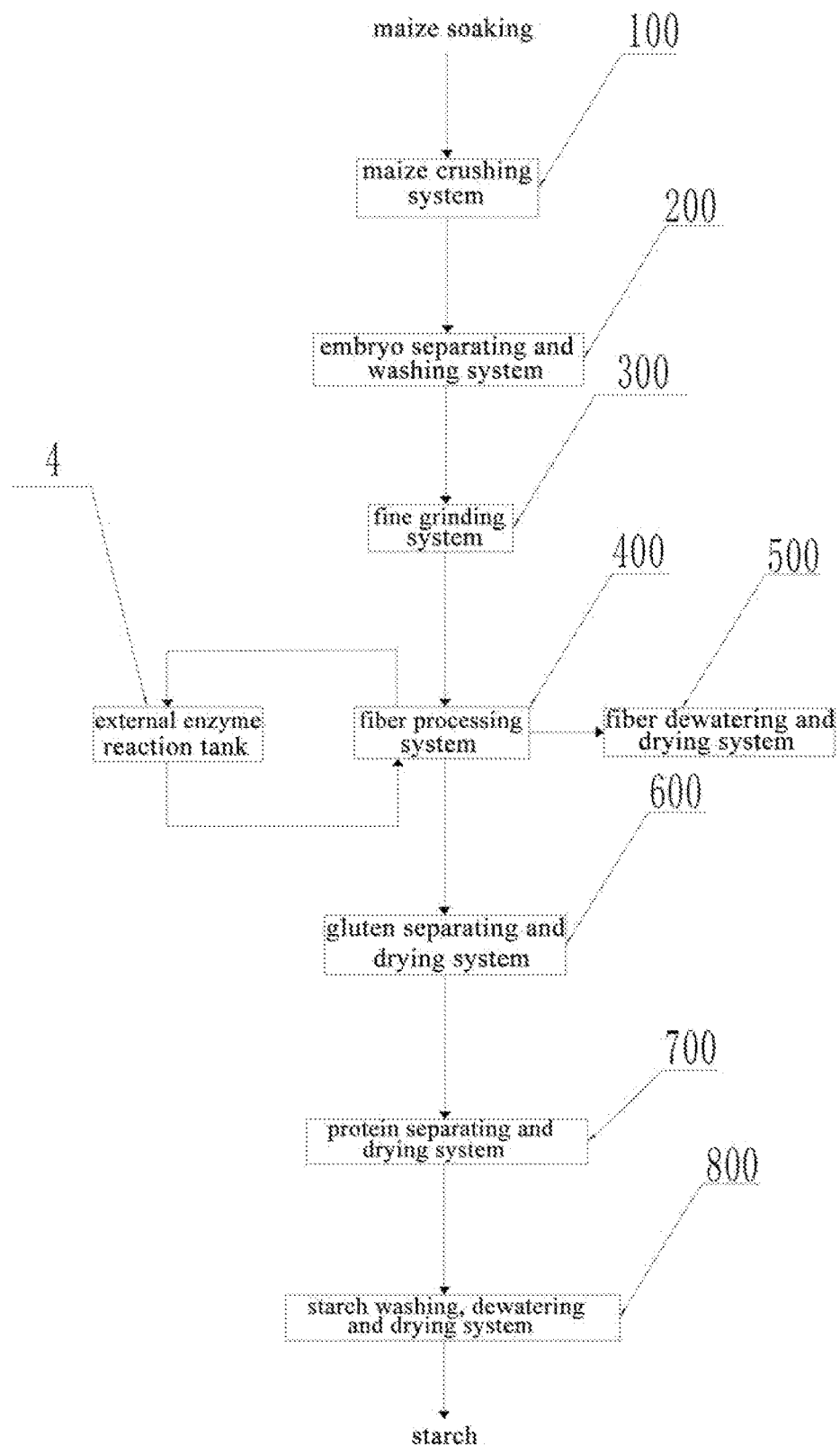
FIG. 19 is a structural schematic diagram of a maize wet-milled starch processing system provided in a particular embodiment of the present application.

As shown in FIG. 19, a particular embodiment of the present application further provides a maize wet-milled starch processing system. The system comprises a maize crushing system 100, an embryo separating and washing system 200, a fine milling system 300, a fiber processing system 400, a fiber dewatering and drying system 500, a gluten separating system 600, a protein separating and drying system 700, and a starch washing, dewatering and drying system 800. The fiber processing system 400 may comprise a pressure curved screen group, a fiber washing sink group, an enzyme preparation adding device, an external enzyme reaction tank, etc. The enzyme preparation adding device, the external enzyme reaction tank, etc. may be the enzyme preparation adding device and the external enzyme reaction tank in the above embodiments. In view of the length, the matching mode between the pressure curved screen group and the fiber washing sink group, and the structures, functions and connection position relationship of the enzyme preparation adding device and the external enzyme reaction tank will not be repeated.

Further, the volume of the external enzyme reaction tank 4 and the flow of the fiber slurry are determined by the daily maize processing capacity of the maize wet-milled starch processing system, for example, for a maize wet-milled starch processing system with the daily processing capacity of 1400 tons of maize, the volume of the external enzyme reaction tank 4 is 290 m$^3$. Before the screen underflow washing water dividing pipe 5 divides screen underflow washing water, the total flow of the fiber slurry entering the external enzyme reaction tank 4 is 150 m$^3$/h; and after the screen underflow washing water dividing pipe 5 divides the screen underflow washing water, the total flow of the fiber slurry entering the external enzyme reaction tank 4 is 105 m$^3$/h.

Further, the volume of the external enzyme reaction tank 4' and the flow of the fiber slurry are determined by the daily maize processing capacity of the maize wet-milled starch processing system, for example, for the maize wet-milled starch processing system with the daily processing capacity of 1500 tons of maize, the volume of the external enzyme reaction tank 4' is 300 m$^3$.

The above is merely the illustrative particular embodiments of the present application, and any equivalent change and modification made by those skilled in the art should fall within the scope of protection of the present application, without departing from the concept and principle of the present application.

The invention claimed is:

1. A maize fiber processing system for extracting maize starch, the system comprising: a pressure curved screen group, a fiber washing sink group, an enzyme preparation adding device and an external enzyme reaction tank, wherein,
    the pressure curved screen group has multiple pressure curved screens, the pressure curved screens separate fiber slurry containing starch and protein into screen overflow and screen underflow, and each of the pressure curved screens has a fiber slurry inlet, a screen overflow outlet and a screen underflow outlet;
    the fiber washing sink group provides a place for washing the fiber slurry by washing water, the fiber washing sink group has multiple fiber washing sinks, and each of the fiber washing sinks has a screen overflow feeding port, a screen underflow feeding port and a discharge port;
    the enzyme preparation adding device adds enzyme preparation into the maize fiber processing system; and
    the external enzyme reaction tank is connected to a discharge port of a middle fiber washing sink, the external enzyme reaction tank receives the fiber slurry in the middle fiber washing sink the fiber slurry is returned back to the fiber slurry inlet of a next pressure curved screen posterior to a middle pressure curved screen through a returning pipe after a predetermined time wherein the screen underflow contains screen underflow washing water, a screen underflow washing water dividing pipe is provided in a second pressure curved screen posterior to the middle pressure curved screen, the screen underflow washing water dividing pipe divides part of the screen underflow washing water, so as to control dry substance concentration in the external enzyme reaction tank, the remaining screen underflow washing water is transported to the screen underflow feeding port of the middle fiber washing sink, and the divided screen underflow washing water flows back into the maize fiber processing system by the screen underflow washing water dividing pipe.

2. The maize fiber processing system according to claim 1, wherein the enzyme preparation adding device is an enzyme preparation adding pipe.

3. The maize fiber processing system according to claim 1, wherein the screen overflow of each of the pressure curved screens in the pressure curved screen group flows to a corresponding fiber washing sink among the fiber washing sink group, and the screen underflow of each of the pressure curved screens in the pressure curved screen group flows to a non-adjacent fiber washing sink to the corresponding fiber washing sink among the fiber washing sink group.

4. The maize fiber processing system according to claim 1, wherein the screen overflow of each of the pressure curved screens in the pressure curved screen group flows to a corresponding fiber washing sink among the fiber washing sink group, and the screen underflow of each of the pressure curved screens in the pressure curved screen group flows to a fiber washing sink one or two sinks apart before the corresponding fiber washing sink among the fiber washing sink group.

5. The maize fiber processing system according to claim 1, wherein a tail end of the screen underflow washing water dividing pipe is connected to the returning pipe.

6. The maize fiber processing system according to claim 1, wherein a tail end of the screen underflow washing water dividing pipe is provided at an upper end of a final discharge port of the external enzyme reaction tank.

7. The maize fiber processing system according to claim 1, wherein a tail end of the screen underflow washing water dividing pipe is connected to the fiber slurry inlet of a next pressure curved screen posterior to the middle pressure curved screen.

8. The maize fiber processing system according to claim 1, wherein a starting end of the screen underflow washing water dividing pipe is provided between the screen underflow outlet and the screen underflow feeding port.

9. The maize fiber processing system according to claim 1, wherein the system further comprises: an external water storage buffer tank provided on the screen underflow washing water dividing pipe.

10. A maize wet-milled starch processing system, wherein the maize wet-milled starch processing system comprises the maize fiber processing system according to claim 1.

11. The maize wet-milled starch processing system according to claim 10, wherein the maize wet-milled starch processing system comprises a maize crushing system, an embryo separating and washing system, a fine grinding system a fiber processing system, a fiber dewatering and drying system, a gluten separating and drying system, a protein separating and drying system, and a starch washing, dewatering and drying system.

12. A maize fiber processing system for extracting maize starch, the system comprising: a pressure curved screen group, a fiber washing sink group, an enzyme preparation adding device and an external enzyme reaction tank, wherein, the pressure curved screen group has multiple pressure curved screens, the pressure curved screens separate fiber slurry containing starch and protein into screen overflow and screen underflow, and each of the pressure curved screens has a fiber slurry inlet, a screen overflow outlet and a screen underflow outlet;

the fiber washing sink group provides a place for washing the fiber slurry by washing water, the fiber washing sink group has multiple fiber washing sinks, and each of the fiber washing sinks has a screen overflow feeding port, a screen underflow feeding port and a discharge port;

the enzyme preparation adding device adds enzyme preparation into the maize fiber processing system; and the external enzyme reaction tank is connected to a screen overflow outlet of a middle pressure curved screen, the external enzyme reaction tank receives the screen overflow in the middle pressure curved screen the screen overflow is returned back to the fiber slurry inlet of a next pressure curved screen posterior to the middle pressure curved screen through a returning pipe wherein the external enzyme reaction tank has an injecting water inlet for adjusting fiber dry substance concentration in the external enzyme reaction tank.

13. The maize fiber processing system according to claim 12, wherein the injecting water inlet is externally connected to an injecting water pipe for adjusting fiber dry substance concentration in the external enzyme reaction tank.

14. The maize fiber processing system according to claim 13, wherein the system further comprises:

a first flow controlling device which is provided at an injecting water inlet and controls an amount of injecting water received by the external enzyme reaction tank.

15. The maize fiber processing system according to claim 14, wherein the system further comprises a washing water injection adjusting device which correspondingly reduces an amount of washing water injected into the maize fiber processing system according to the amount of injecting water so as to keep a total amount of water in the maize fiber processing system unchanged.

16. The maize fiber processing system according to claim 12, wherein the system further comprises:

a second flow controlling device which is provided at a washing water inlet of the maize fiber processing system and controls the water inflow amount of external washing water of the maize fiber processing system.

17. The maize fiber processing system according to claim 12, wherein the enzyme preparation adding device is an enzyme preparation adding pipe.

* * * * *